(12) United States Patent
Bederson

(10) Patent No.: US 11,439,413 B2
(45) Date of Patent: Sep. 13, 2022

(54) EPIDURAL/SUBDURAL MINIMALLY INVASIVE ACCESS TOOL

(71) Applicant: Icahn School of Medicine at Mount Sinai, New York, NY (US)

(72) Inventor: Joshua Bederson, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 183 days.

(21) Appl. No.: 16/764,520

(22) PCT Filed: Nov. 16, 2018

(86) PCT No.: PCT/US2018/061590
§ 371 (c)(1),
(2) Date: May 15, 2020

(87) PCT Pub. No.: WO2019/099881
PCT Pub. Date: May 23, 2019

(65) Prior Publication Data
US 2020/0367915 A1    Nov. 26, 2020

Related U.S. Application Data

(60) Provisional application No. 62/588,031, filed on Nov. 17, 2017.

(51) Int. Cl.
*A61B 17/17* (2006.01)
*A61B 17/16* (2006.01)

(52) U.S. Cl.
CPC ...... *A61B 17/1739* (2013.01); *A61B 17/1695* (2013.01)

(58) Field of Classification Search
CPC ... A61B 17/1695; A61B 17/17; A61B 17/171; A61B 17/1732; A61B 17/1739
See application file for complete search history.

(56) References Cited

U.S. PATENT DOCUMENTS

| | | | |
|---|---|---|---|
| 5,201,742 A * | 4/1993 | Hasson | A61B 17/3403 606/1 |
| 5,207,681 A * | 5/1993 | Ghadjar | A61B 17/1695 606/180 |
| 6,206,885 B1 * | 3/2001 | Ghahremani | A61B 17/1695 128/DIG. 26 |
| 6,267,769 B1 * | 7/2001 | Truwit | A61B 90/11 606/1 |
| 6,752,812 B1 * | 6/2004 | Truwit | A61B 90/11 606/1 |

(Continued)

FOREIGN PATENT DOCUMENTS

WO    WO 2012/158254    11/2021

*Primary Examiner* — Eric S Gibson
(74) *Attorney, Agent, or Firm* — Leason Ellis LLP

(57) ABSTRACT

A cranial drill guide includes a housing and a drill guide sleeve assembly pivotally attached to the housing. The drill guide sleeve assembly has at least two degrees of freedom to allow the drill guide sleeve assembly to be moved to a first pivoted position for forming an angled burr hole through a cranial surface. The two degrees of freedom can comprise a pivoting motion of the drill guide sleeve assembly and an axial motion of a portion of the drill guide sleeve assembly.

27 Claims, 24 Drawing Sheets

(56) References Cited

U.S. PATENT DOCUMENTS

| | | | | |
|---|---|---|---|---|
| 7,217,276 B2* | 5/2007 | Henderson | A61B 90/36 | 606/130 |
| 7,736,371 B2* | 6/2010 | Schoepp | A61B 17/3403 | 606/130 |
| 8,747,418 B2* | 6/2014 | Qureshi | A61B 90/11 | 606/130 |
| 9,192,446 B2* | 11/2015 | Piferi | A61B 90/11 | |
| 10,426,375 B2* | 10/2019 | Bankiewicz | A61B 90/11 | |
| 10,881,467 B2* | 1/2021 | Lenarz | A61B 34/20 | |
| 11,013,531 B2* | 5/2021 | McIntyre | A61B 17/3421 | |
| 2002/0049451 A1* | 4/2002 | Parmer | A61B 90/11 | 606/108 |
| 2003/0040753 A1* | 2/2003 | Daum | A61B 17/3462 | 606/96 |
| 2003/0055436 A1* | 3/2003 | Daum | A61B 90/11 | 606/130 |
| 2003/0114876 A1* | 6/2003 | Samset | A61B 34/20 | 606/172 |
| 2004/0167543 A1* | 8/2004 | Mazzocchi | A61B 90/11 | 606/130 |
| 2006/0229641 A1* | 10/2006 | Gupta | A61B 17/3403 | 606/130 |
| 2007/0106305 A1* | 5/2007 | Kao | A61B 90/39 | 606/130 |
| 2010/0042111 A1* | 2/2010 | Qureshi | F16M 11/36 | 606/130 |
| 2014/0024927 A1* | 1/2014 | Piferi | A61B 17/1739 | 600/417 |
| 2014/0066750 A1* | 3/2014 | Piferi | A61B 90/11 | 600/417 |
| 2015/0202011 A1* | 7/2015 | Gowda | A61B 90/11 | 606/130 |
| 2016/0000448 A1* | 1/2016 | Houssiere | A61B 17/1622 | 606/130 |
| 2017/0151032 A1* | 6/2017 | Loisel | A61B 90/10 | |
| 2018/0110568 A1* | 4/2018 | Lenarz | A61B 17/1771 | |
| 2018/0206883 A1* | 7/2018 | McIntyre | A61B 17/3421 | |
| 2020/0367915 A1* | 11/2020 | Bederson | A61B 17/1739 | |

* cited by examiner

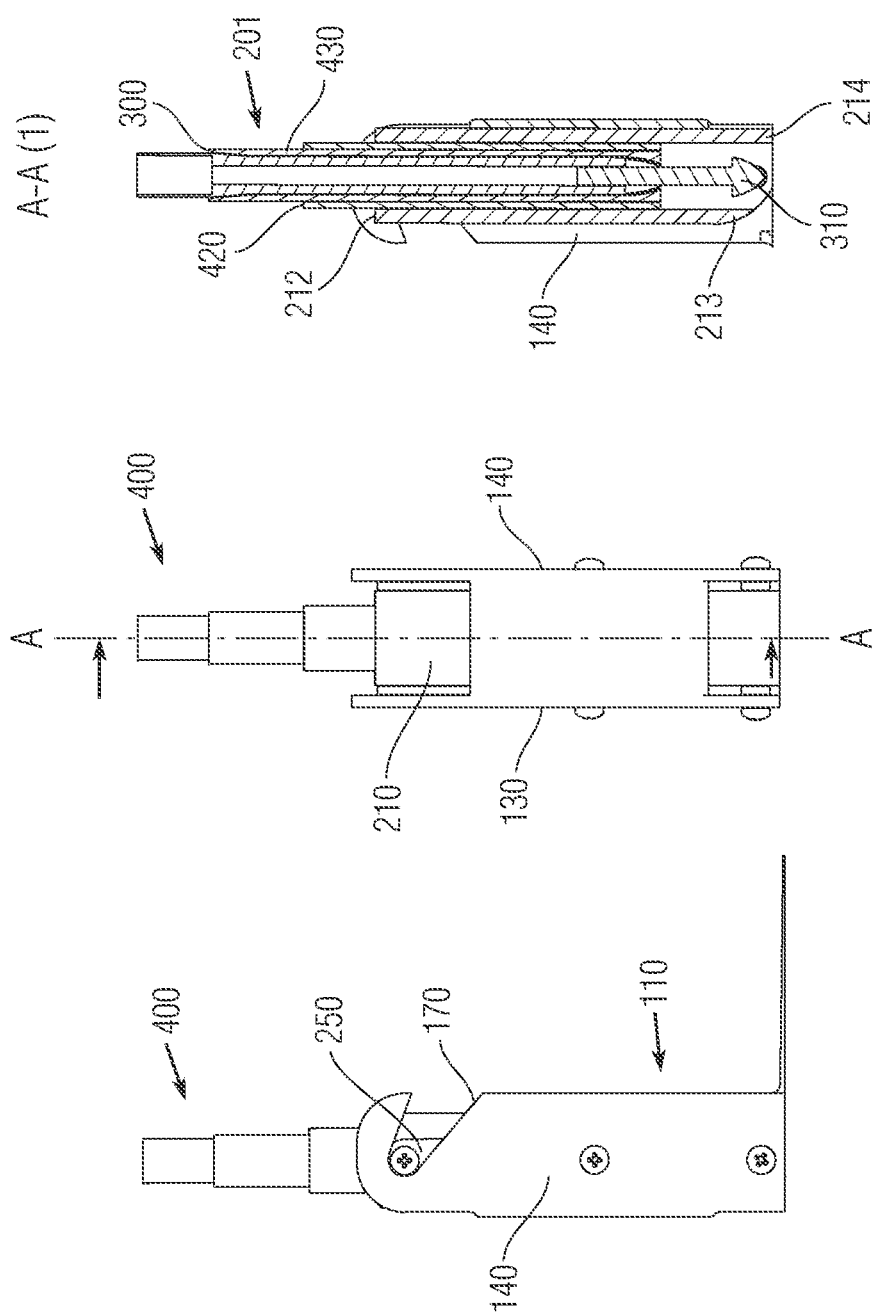

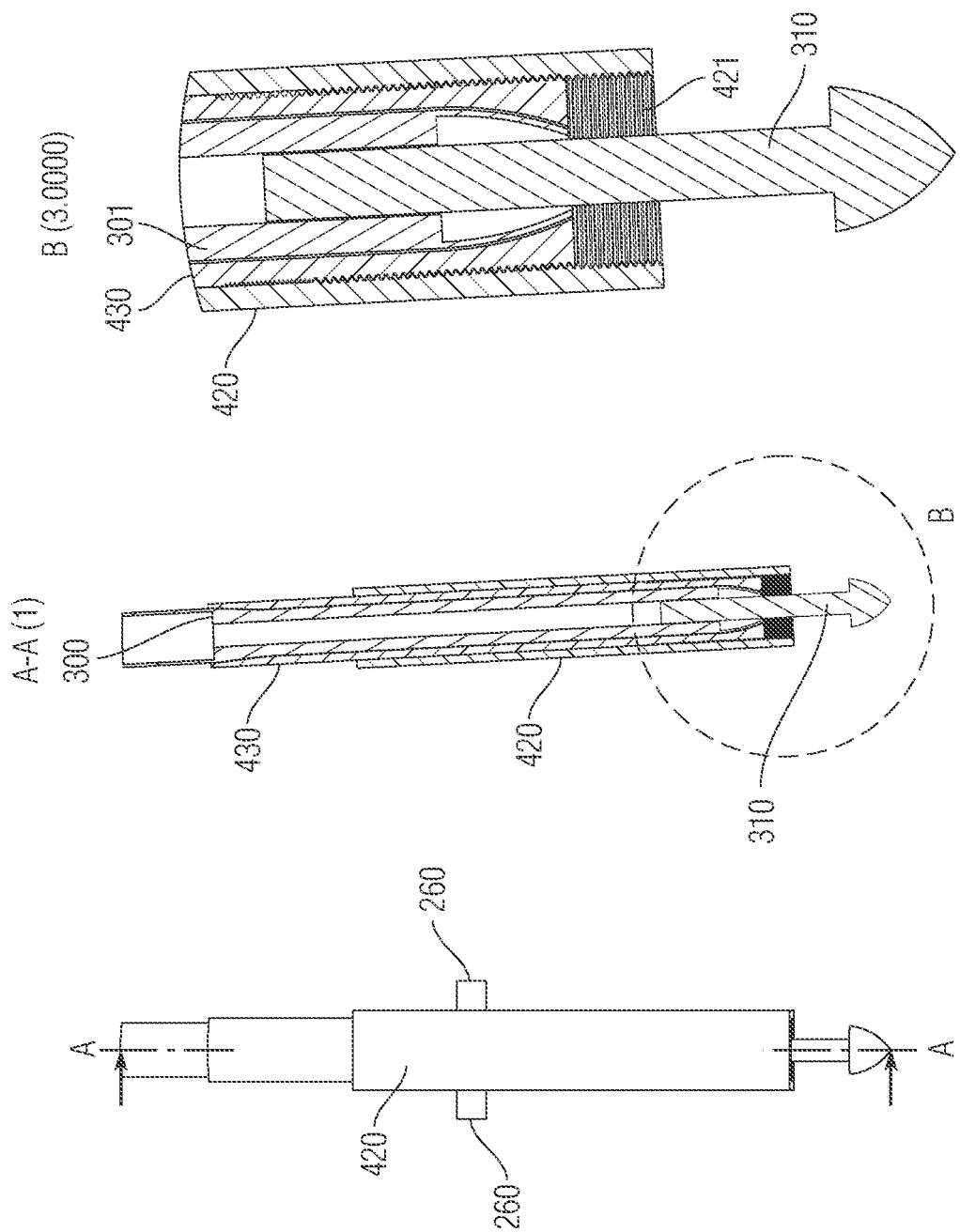

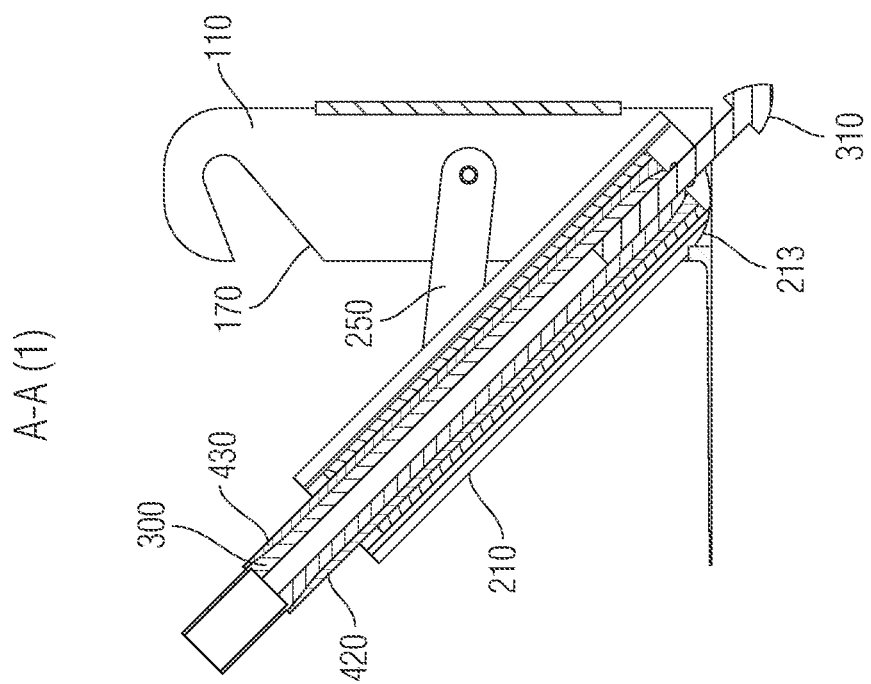

EPIDURAL/SUBDURAL MINIMALLY INVASIVE ACCESS TOOL

CROSS REFERENCE TO RELATED APPLICATION

The present application is a U.S. National Phase Application under 35 U.S.C. § 371 of International Patent Application No. PCT/US2018/061590, filed Nov. 16, 2018, which claims the priority to and the benefit of U.S. Patent Application No. 62/588,031, filed Nov. 17, 2017, each of which is incorporated by reference as if expressly set forth in their respective entirety herein.

TECHNICAL FIELD

The present invention is directed to a tool used in a neurosurgical procedure and more particularly, relates to a mechanical drill guide that is used to restrict and direct the movement of a high-speed cranial drill to create an angled burr hole through cortical bone to allow for epidural or subdural placement of an electrode.

BACKGROUND

As is well known, the brain is surrounded by a layer of tissue called the meninges which lies below the skull (cranium). The meninges are thus the coverings of the brain. They protect the brain by housing a fluid-filled space, and they function as a framework for blood vessels. The meninges have three layers: the dura mater, the arachnoid mater, and the pia mate". The arachnoid mater is attached to the pia mater by arachnoid trabeculae, which is a web-like matrix of connective tissue. The space between the two layers, the subarachnoid space, is filled with cerebrospinal fluid (CSF). Pressure from the cerebrospinal fluid presses the arachnoid mater against the dura mater and the pia mater adheres to the surface of the brain.

Craniotomy is a surgery to cut a bony opening in the skull. A section of the skull, called a bone flap, is removed to access the brain underneath. There are many types of craniotomies, which are named according to the area of skull to be removed. Typically, the bone flap is replaced. If the bone flap is not replaced, the procedure is called a craniectomy. Craniotomies are also named according to their size and complexity. Small dime-sized craniotomies are called burr holes or keyhole craniotomies, and even small openings are called "twist trill" opening. Sometimes stereotactic frames, image-guided computer systems, robotics or endoscopes are used to precisely direct instruments through these small openings. Burr holes and twist drill openings or keyhole craniotomies are used for minimally invasive procedures to perform any number of different procedures, including but not limited to: 1) insert a shunt into the ventricles to drain cerebrospinal fluid (hydrocephalus); 2) insert a deep brain stimulator to treat Parkinson Disease; 3) insert an intracranial pressure (ICP) monitor; 4) remove a small sample of abnormal tissue (needle biopsy); 5) drain a blood clot (stereotactic hematoma aspiration); and 6) insert an endoscope to remove small tumors and clip aneurysms.

Intracranial electrodes are used to detect normal and abnormal electrical activity of the brain. "Deep Brain" electrodes are typically placed through a burr hole or twist drill opening using computer-guided and robotic-assisted. When brain electrodes are placed, burr holes and twist drill openings are generally used to direct electrodes and catheters deep into the brain as opposed to on the cortical surface. This is because the thickness of the skull (approximately 8.1 mm on average) restricts the angle of the catheter delivery system to a near-perpendicular orientation with respect to the bone surface. When cortical surface electrodes are required, these are typically placed through larger craniotomies performed in the operating room under general anesthesia.

Use of a bur hole for placement of an epidural or subdural electrode is risky, because the shape of the narrow opening directs the electrode into the brain tissue, as opposed to along the surface. This is why surface electrodes are generally placed though larger openings that permit a tangential angle between the electrode and the brain surface. If an angled burr hole or twist drill opening could be created safely it might be possible to avoid the larger openings and general anesthesia. However, several challenges have made this difficult to achieve.

For traditional burr holes and twist drill access, the surgeon relies upon visual and sensory feedback to determine the appropriate angle and depth of the cranial drilling procedure. While this technique is successful for standard perpendicular openings, there are a number of disadvantages that would make it unsafe to attempt angled openings that would permit placement of surface subdural or epidural electrodes. The present invention overcomes these disadvantages and provides an improved means for rapidly and safely creating an angled burr hole.

As is understood, the term epidural refers to the region between the skull (cranium) and the dura, whereas, the term "subdural" refers to the region between the dura and the arachnoid which lies below the dura. As discussed herein, the drill guide of the present invention is configured for forming an angled burr hole that permits both cortical epidural electrode placement and cortical subdural electrode placement.

SUMMARY

In accordance with one embodiment, a cranial drill guide includes a housing and a drill guide sleeve assembly pivotally attached to the housing. The drill guide sleeve assembly has at least two degrees of freedom to allow the drill guide sleeve assembly to be moved to a first pivoted position for forming an angled burr hole to a specified depth through the cranium. The two degrees of freedom can comprise a pivoting motion of the drill guide sleeve assembly and an axial motion of a portion of the drill guide sleeve assembly. The pivoting motion determines the angle of the burr hole while the axial motion determines the depth of the burr hole. The drill guide sleeve assembly can comprise an outer sleeve and an inner sleeve. The outer sleeve is pivotally coupled to the housing about a first pivot axis, while the inner sleeve moves axially within the outer sleeve in response to the pivoting of the outer sleeve.

BRIEF DESCRIPTION OF THE DRAWING FIGURES

FIG. 20 is a side elevation view of a cranial drill guide according to one exemplary embodiment in a fully retracted position;

FIG. 21 is a rear elevation view thereof;

FIG. 22 is a cross-sectional view taken along the line A-A in FIG. 21;

FIG. 23 is a side elevation view of a depth adjustment mechanism associated with a drill sleeve assembly;

FIG. 24 is a cross-sectional view taken along the line A-A of FIG. 23;

FIG. 25 is an enlarged view of distal tip portion of the cross-sectional view of FIG. 24;

FIG. 32 is a cross-sectional view taken along the line A-A in FIG. 21.

DETAILED DESCRIPTION OF CERTAIN EMBODIMENTS

Figure 1:
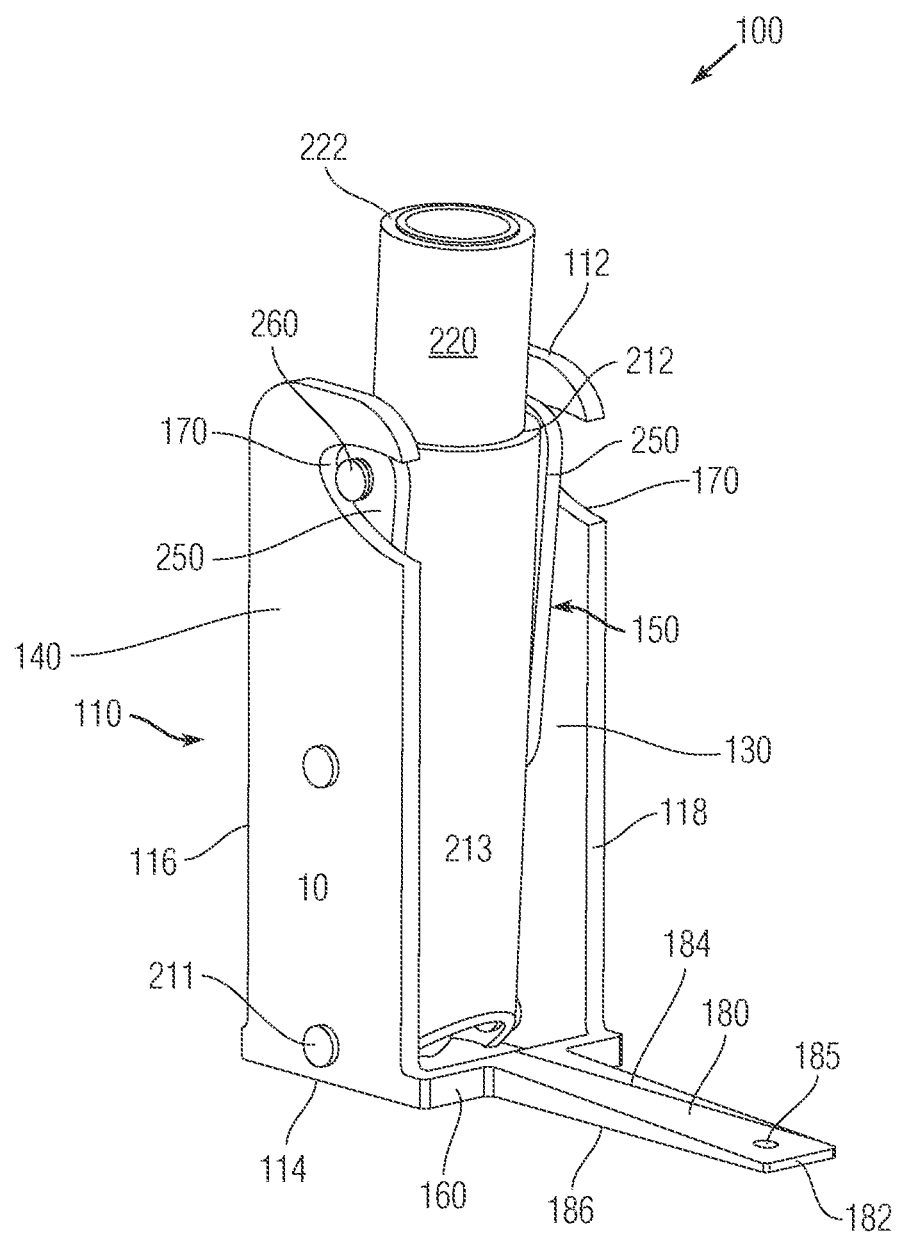
FIG. 1 is a rear and side perspective view of a cranial drill guide according to one exemplary embodiment of the present invention showing the drill guide in a fully retracted position.

The apparatuses and methods are not limited in any way to the illustrated embodiments and/or arrangements as the illustrated embodiments and/or arrangements described below are merely exemplary of the present apparatuses and methods, which can be embodied in various forms as appreciated by one skilled in the art. Therefore, it is to be understood that any structural and functional details disclosed herein are not to be interpreted as limiting the present application, but rather are provided as a representative embodiment and/or arrangement for teaching one skilled in the art one or more ways to implement the present apparatuses and/or methods. Moreover, just because a certain feature is depicted in combination with a particular set of other features, no intent to so limit the invention can be inferred and each feature can be combined with any other set of other features.

Implanted EEG electrodes are often necessary to pinpoint the origin of seizure activity. They are particularly helpful for more precisely localizing seizure activity that has been identified with scalp EEG recordings. For example, the scalp recordings may determine that seizures arise from the right hemisphere. Implanted EEG electrodes can then reveal whether the epileptogenic activity arises specifically from the frontal lobe, rather than the temporal, parietal, or occipital lobes. These invasive electrodes allow EEG recording directly from the surface of the brain or from deeper cortical structures.

Implanted EEG electrodes also can be used to stimulate the brain and map cortical and subcortical neurologic functions, such as motor or language function, in preparation for epilepsy surgery. This information is then used in conjunction with the seizure data to determine the risk-benefit profile of the surgery. In some cases, the stimulation of electrodes may trigger auras or seizures during this functional mapping session.

There are two main categories of implanted electrodes: subdural electrodes and stereotaxic depth electrodes.

Conventional cranial drill guides are configured to drill a perpendicular (vertical) hole through the cortical bone (e.g., cranium) to allow for insertion of depth electrodes; however, this type of hole does not allow for either epidural insertion or subdural insertion of a surface electrode since the elongated surface electrode cannot bend a sufficient degree (i.e., a 90 degree bend) to allow placement in these locations from a vertical drill hole. In contrast, by forming an angled burr hole in accordance with the present teachings, the elongated surface electrode can be inserted through the angled burr hole and then "snaked" into the desired epidural or subdural position.

Now referring to FIGS. 1-14, a cranial drill guide 100 is illustrated and is configured to restrict and direct the movement of a high speed cranial drill 300 to create an angled burr hole that is configured to permit passage of an electrode (e.g., surface electrode) to an epidural or subdural location. The shape and position of the burr hole can then be used to place an epidural or subdural electrode of catheter to measure electrical activity, pressure or other parameters from the brain surface. As described herein, the drill guide 100 permits creation of the burr hole rapidly and safely at the bedside or similar location and solves the problem that typically this procedure requires a craniotomy in the operating room. As a result of the drill guide's construction, local anesthesia (e.g. lidocaine) can be used. As described herein, the drill guide 100 provides a number of advantageous features, including but not limited to, the drill guide 100 being reversible/removable, the (hill guide 100 permits directional control at the time of insertion, the drill guide 100 is convertible in or can be permanently implanted, and stereotactic guidance with electromagnetic (EM) technology.

The drill guide 100 includes a housing 110 that has a first end 112, an opposing second end 114, a forward edge 116, and a rear edge 118. The housing 110 can also be thought of as including a first side and an opposing second side. The first end 112 can be thought of as being a top or upper end, while the second end 114 can be thought of as being a bottom or lower end.

As shown, the housing 110 can be defined by a first side wall 130 that defines the first side of the housing 110 and an opposing second side wall 140 that defines the second side of the housing 110. The first side wall 130 and second side wall 140 are spaced apart from one another so as to define a space 150 therebetween, with the first side wall 130 being connected to the second side wall 140 by a cross or transverse wall 160. As shown, the cross wall 160 connects the bottom (second) end 114 of the first side wall 130 to the bottom (second) end 114 of the second side wall 140. The cross wall 160 is located along the rear edge 118.

Proximate the first end 112 of each of the first side wall 130 and the second side wall 140, a notch 170 can be formed therein. The notch 170 is open along the rear edge 118. The edges of the notch 170 can be arcuate in shape, with the notch 170 being widest at its opening along the rear edge 118. The notch 170 limits the degree of travel of the drill guide sleeve assembly 200 in one direction. It will be appreciated that the notch 170 can be eliminated which simply can result in the height of the housing being less than the embodiment that is illustrated. For example, when the notch 170 is eliminated, each of the first side wall 130 and the second side wall 140 can terminate at first end 112 that can be located just below where the notch 170 is formed.

As discussed herein, it will be appreciated that the notch 170 can be eliminated as a result of the length of the housing 110 being reduced.

Along a rear edge of the cross wall 160, an extension or finger 180 is formed and extends outwardly therefrom. The extension 180 can be a linear structure defined by a free end 182, a top surface 184, and an opposing bottom surface 186. The bottom surface 186 can be a planar surface and can be coplanar with the planar bottom of the cross wall 160. As shown, the top surface 184 can be an angled surface such that the extension 180 is thickest where the extension 180 joins the cross wall 160. Proximate the free end 182, there is a through hole 185.

The drill guide 100 also includes a movable drill guide sleeve assembly 200 that guides a drill bit 310, as well as the lower portion, of a high speed cranial drill 300. The drill guide sleeve assembly 200 is pivotally coupled to the housing 110 and is movable between at least two different positions. The drill guide sleeve assembly 200 includes an outer sleeve 210 that is pivotally attached to an inner face of each of the first side wall 130 and the second side wall 140. The outer sleeve 210 has a first end 212 and an opposing second end 214. The first end 212 can be thought of has being a top end and the second end 214 being a bottom end. The outer sleeve 210 is pivotally coupled to the housing 110 at or proximate the second end 214.

Figure 4:
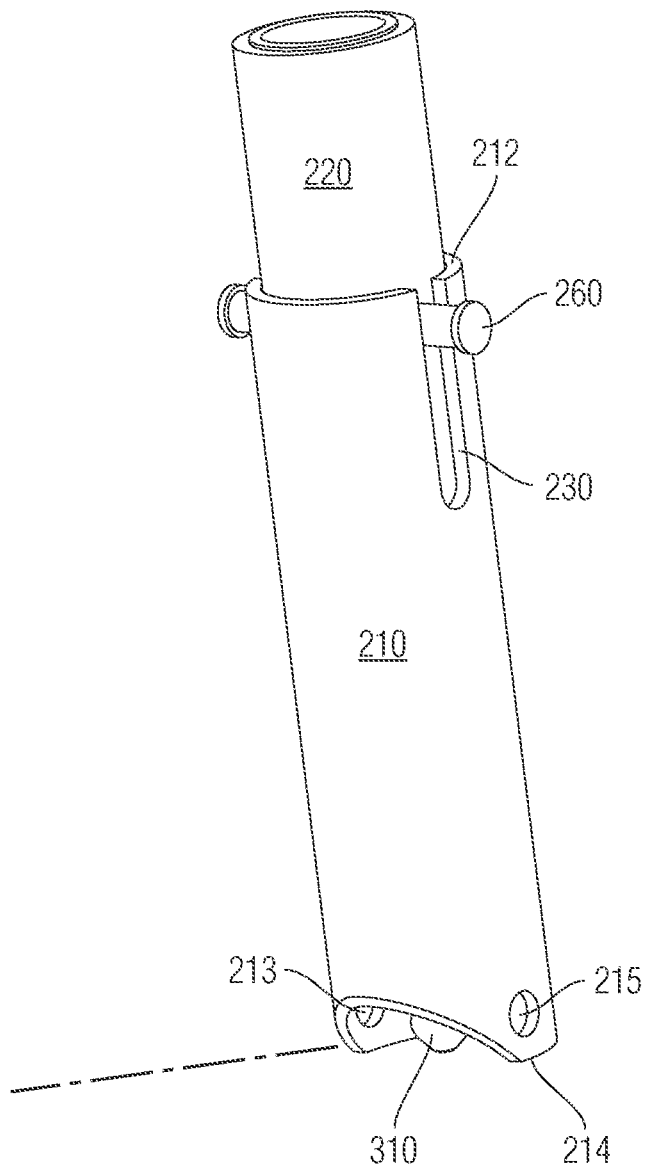
FIG. 4 is a side perspective view of a drill guide sleeve assembly formed of an inner sleeve and an outer sleeve.
Figure 5:
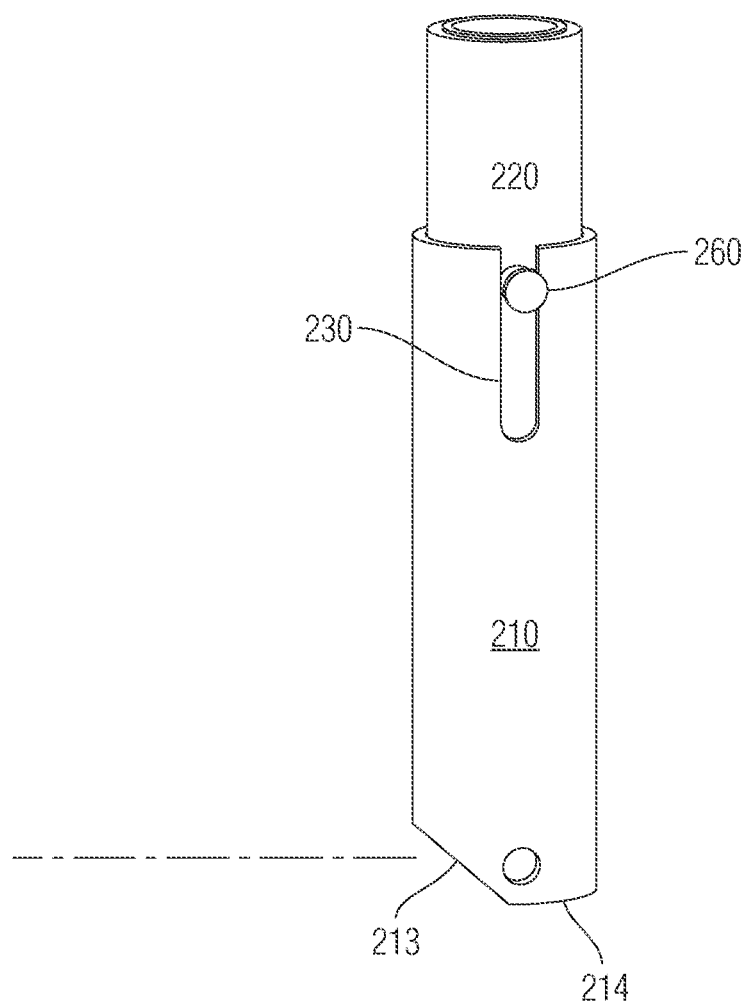
FIG. 5 is another side perspective view thereof.
Figure 6:
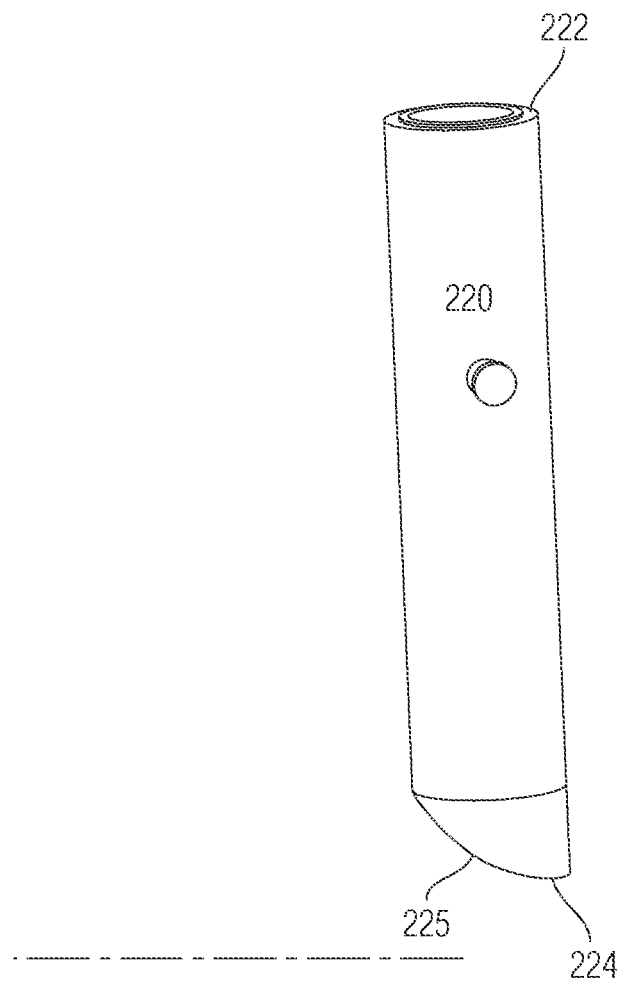
FIG. 6 is a side perspective view of the inner sleeve.

As illustrated, the outer sleeve 210 is generally cylindrical in shape to accommodate the round drill bit 310; however, other shapes are equally possible. Any number of different types of coupling techniques can be used to pivotally couple the outer sleeve 210 to the housing 110. For example, as shown, the outer sleeve 210 can mate to a pair of pins or posts 211 that are oriented 180 degrees from one another and are oriented perpendicular to the outer sleeve 210 so as to face the inner faces of the first side wall 130 and the second side wall 140. Each of the first side wall 130 and the second side wall 140 includes a hole that receives one pin 211 and as shown in FIG. 4, the outer sleeve 210 includes holes 215 to permit the outer sleeve 210 to be pivotally coupled to the housing 110. The holes are formed proximate the bottom end 114 of each of the first side wall 130 and the second side wall 140. The cylindrical shaped outer sleeve 210 is thus contained between the first side wall 130 and the second side wall 140.

Figure 2:
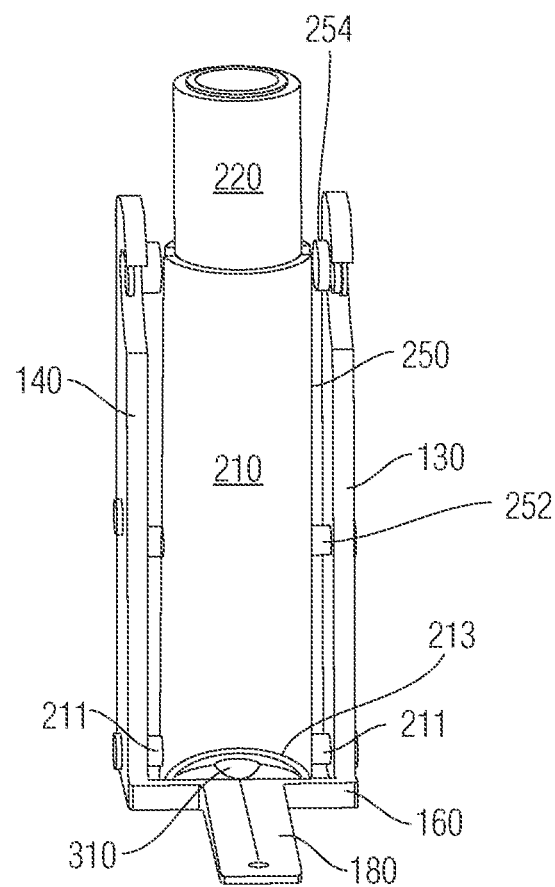
FIG. 2 is a rear perspective view thereof.
Figure 10:
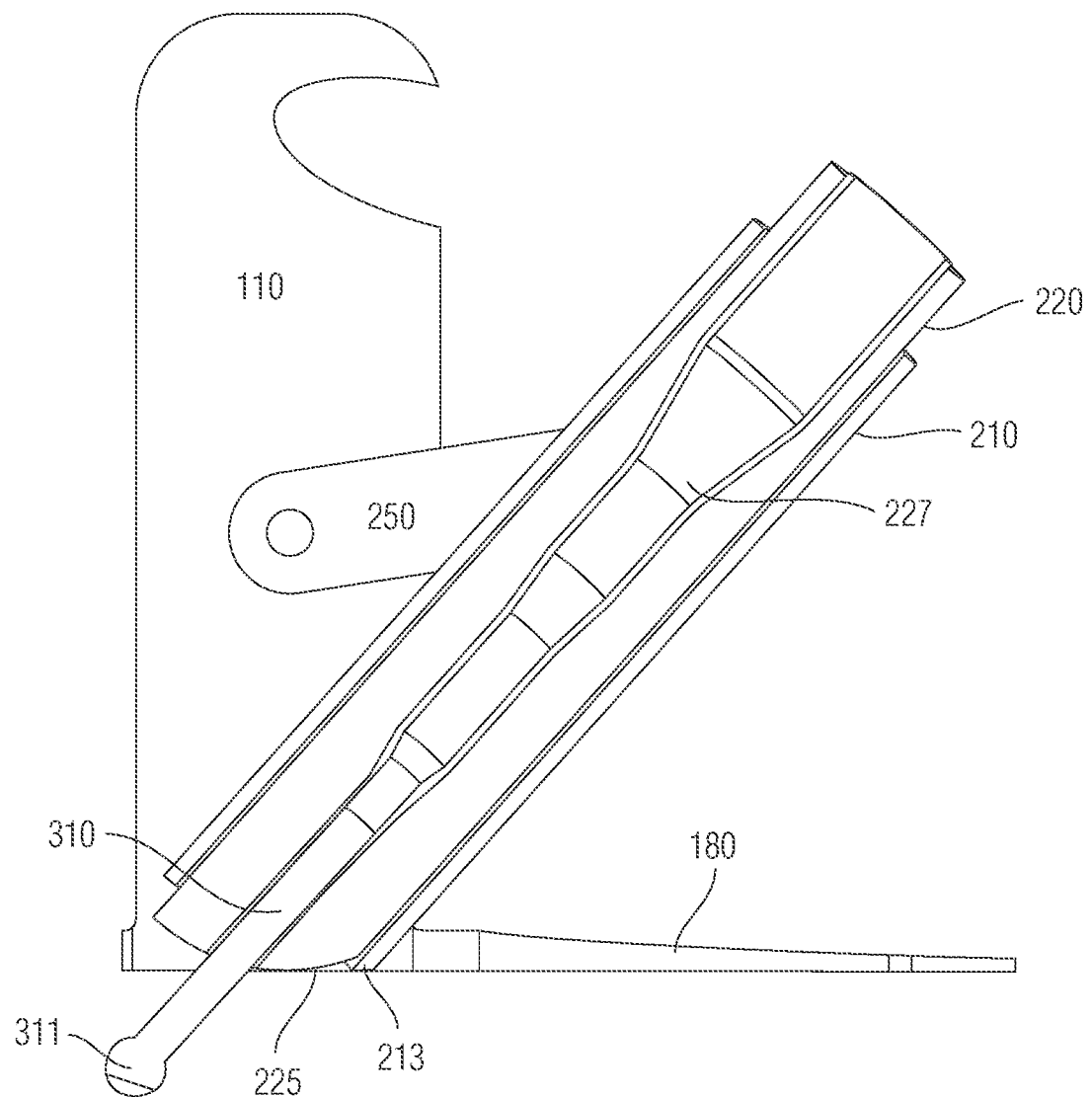
FIG. 10 is a cross-sectional side elevation view thereof.
Figure 11:
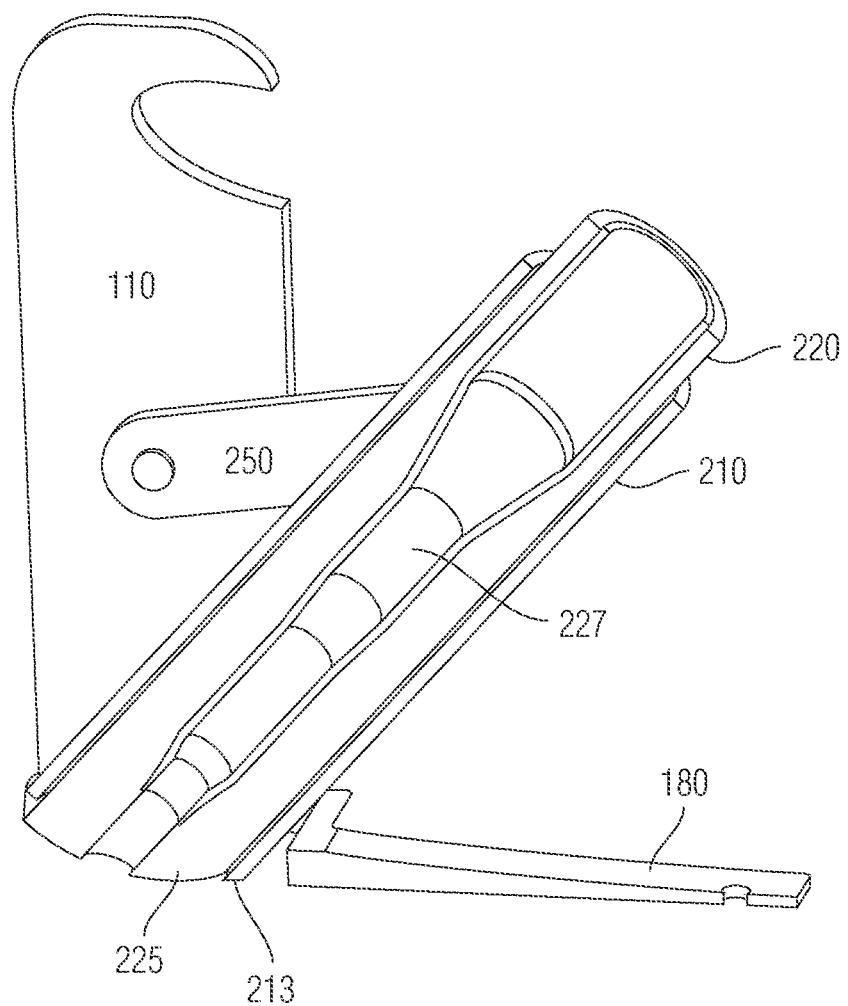
FIG. 11 is a side view, in cross-section, of the drill guide in the fully extended position.
Figure 12:
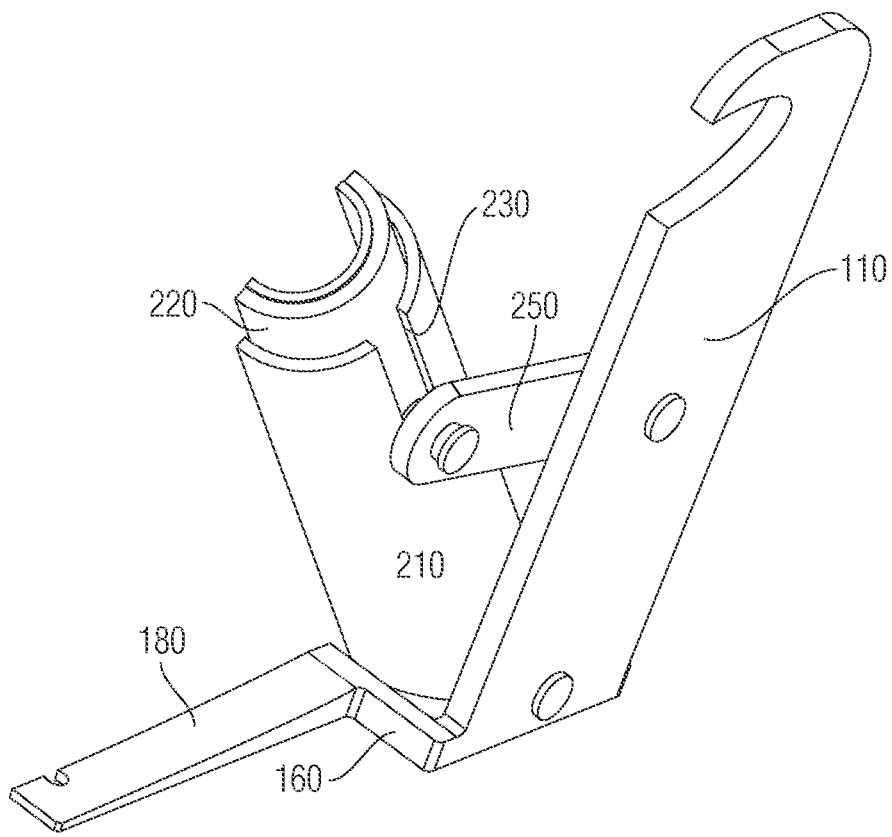
FIG. 12 is a side perspective view, in cross-section, of the drill guide in the fully extended position.

As shown in FIGS. 1, 2 and 4, the bottom edge 214 of the outer sleeve 210 is preferably contoured to accommodate the operation of the drill guide sleeve assembly 200 as described herein in detail. More particularly, the bottom edge 214 of the outer sleeve 210 is not contained in a single plane but instead, the bottom edge 214 contains a first portion that is contained within a single plane and a second portion which represents an upwardly sloped portion 213 relative to the other portion. The portion 213 thus has an arcuate shaped bottom edge that is sloped relative to the flat portion of the bottom edge 214. The upwardly sloped portion 213 is the portion at the bottom edge 214 that is lowered towards the bottom of the housing 110 as the drill guide sleeve assembly 200 is moved to a fully extended (in-use) position as described herein (as illustrated, the upwardly sloped portion 213 faces the extension 180). In the vertical (at rest) position (FIG. 1), the upwardly sloped portion 213 is thus raised relative to the opposite portion of the bottom edge 214 in that the bottom edge of the outer sleeve 210 slopes upwardly from the opposite portion to the portion 213. Thus, the upwardly sloped portion 213 is located where there could be impingement with the cortical bone in the pivoted (fully extended) position (FIG. 10).

The outer sleeve 210 has a pair of opposing slots 230 formed therein at a first (top) end 212 of the outer sleeve 210. The slots 230 are thus 180 degrees apart and are open at the first end 212. Each slot 230 is closed ended (at an opposite second end) and extends in a linear manner.

The drill guide sleeve assembly 200 also includes an inner sleeve 220. The inner sleeve 220 is configured so as to be axially movable within the outer sleeve 210. The inner sleeve 220 can also be cylindrical in shape to accommodate the drill bit 310. The inner sleeve 220 can includes an open top end (edge) 222 and an open bottom end (edge) 224.

The inner sleeve 220 is also pivotally coupled to the housing 110 by means of linkages 250. Each linkage 250 is an elongated structure that has a first end 252 and an opposing second end 254. The first ends 252 of the two linkages 250 are pivotally coupled to the opposing inner surfaces of the first side wall 130 and the second side wall 140. As shown, a rivet 10 or the like can be used to pivotally attach the linkages 250 to the first side wall 130 and the second side wall 140. As shown, the attachment location of the linkages 250 to the first side wall 130 and the second side wall 140 is above the attachment location of the outer sleeve 210 to the first side wall 130 and the second side wall 140.

The second ends 254 of the two linkages 250 are pivotally coupled to the inner sleeve 220. More specifically, the coupling members 260, e.g., pins or rivets, that connect the linkages 250 to the inner sleeve 220 pass through the slots 230. The slots 230 thus allow access to the inner sleeve 220 that is contained within the hollow center of the outer sleeve 210. The closed end of the slot 230 defines a stop and thus defines a maximum degree of travel of pin 260. As will be appreciated in view of the figures, as the outer sleeve 210 pivots relative to the housing 110, the coupling members 260 ride within the slots 230 in a first direction when the outer sleeve 210 (and the contained inner sleeve 220) are pivoted in a first direction and in an opposite second direction when the outer sleeve 210 (and the contained inner sleeve 220) are pivoted in a second direction.

It will be appreciated that the inner sleeve 220 is not directly attached to the outer sleeve 210 since the inner sleeve 220 needs to move axially within the outer sleeve 210 during the pivoting motion of the outer sleeve 210.

It will further be appreciated that the because the inner sleeve 220 moves axially within the outer sleeve 210, the relative position of the inner sleeve 220 changes relative to the outer sleeve 210. According to at least one embodiment of the present invention, the amount of the inner sleeve 220 that protrudes above the top end of the outer sleeve 210 changes according to the position of the outer sleeve 210 relative to the housing 110 (it is also possible that in the rest position, the inner sleeve 220 does not protrude above the top of the outer sleeve 210). In particular, when the coupling members 260 are located closer to the open ends of the slots 230, the inner sleeve 220 protrudes a maximum distance above the top end of the outer sleeve 210. Conversely, when the coupling members 260 are at or close to the closed ends of the slots 230, the inner sleeve 220 protrudes a minimum distance above the top end of the outer sleeve 210 or does not protrude above the top end of the outer sleeve 210 at all. In one embodiment, it is also possible in the storage position (vertical position) that the inner sleeve 220 does not extend above the top end of the outer sleeve 210.

Figure 3:
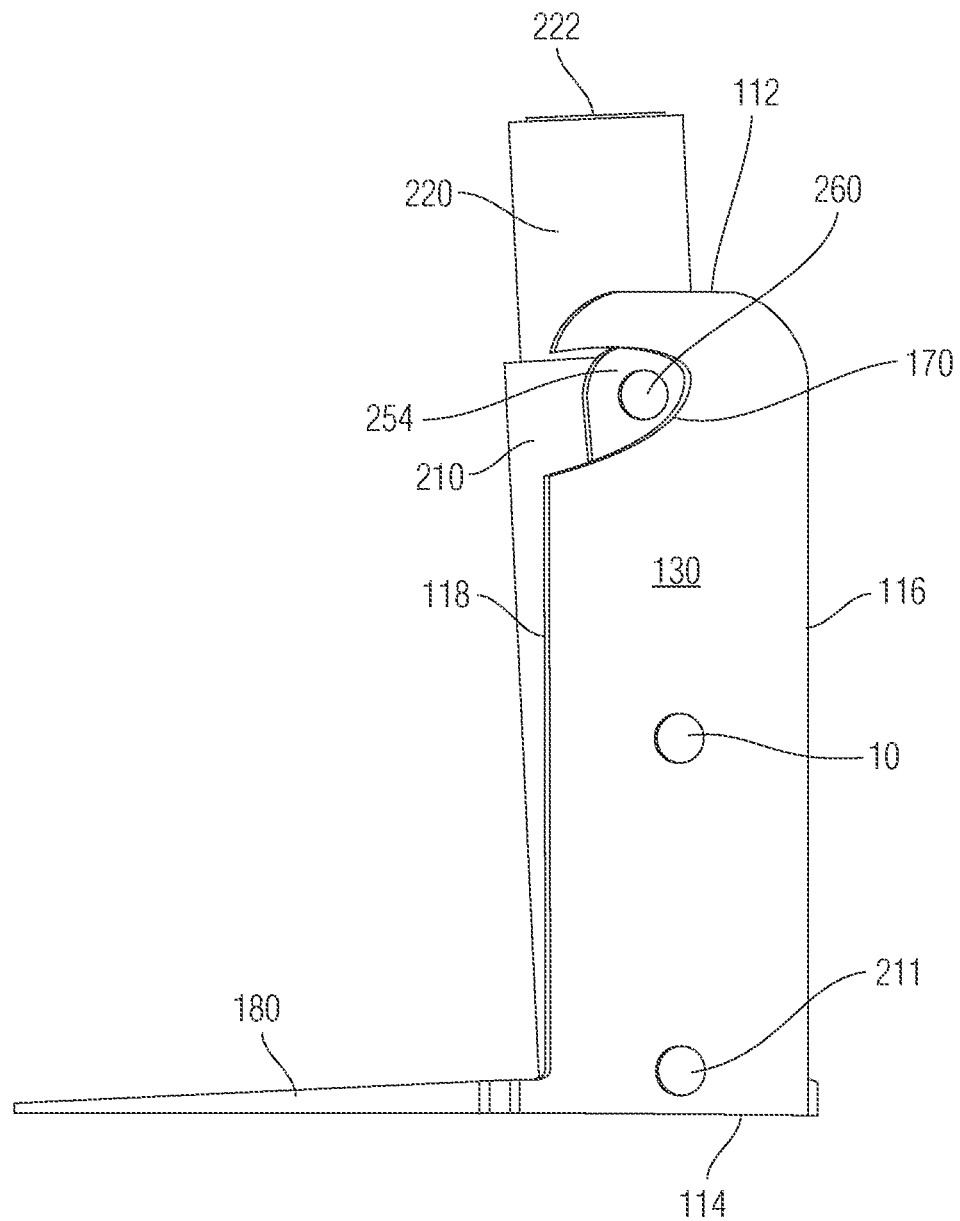
FIG. 3 is a side elevation view thereof.

In one embodiment, the outer sleeve 210 and inner sleeve 220 move between at least a first position which is a vertical position in which the outer sleeve 210 and inner sleeve 220 are fully contained within the housing 110 and a second position which is an angled position in which the outer sleeve 210 and inner sleeve 220 are at a set angle relative to a longitudinal axis of the housing 110. FIGS. 1-3 show the drill guide sleeve assembly 200 in a fully retracted position, while FIGS. 9-12 show the drill guide sleeve assembly 200 in the extended (fully pivoted) position.

One skilled in the art will readily appreciate that when the drill guide sleeve assembly 200 is moved to the fully extended (fully pivoted) position, it will remain in this position in normal use due to gravitational force (the weight of the drill guide sleeve assembly). Similarly, when the drill guide sleeve assembly 200 is in the first position, it which it lies vertically, the drill guide sleeve assembly 200 similarly can be maintained in this position. In one embodiment, the drill guide sleeve assembly 200 is intended to be placed only in the first position, which is a storage position, and the second position (FIG. 9), which is an in-use position.

It will also be appreciated a lock mechanism can be incorporated into the drill guide design to allow the drill guide sleeve assembly 200 to be releasably locked in a plurality of positions, including the first (storage) position and the second (fully pivoted position). Moreover, the lock mechanism can lock the drill guide sleeve assembly 200 in one or more intermediate positions between the first position and the second position. For example, a removable fixed pin can be installed into a hole in the housing to act as a hard stop and prevent any additional downward pivoting of the assembly 200. It will be appreciated that as the drill guide sleeve assembly 200 pivots, the inner sleeve 220 lowers within the outer sleeve 210, and this controls the permitted drill depth of the drill bit 310 beyond the bottom end of the outer sleeve 210 which is necessary it will be readily understood that the length of a perpendicular burr holes is less than a length of an angled burr hole formed in accordance with the present invention. Since the length of the angled burr hole is greater, a longer drill bit 310 is required to pass through the cortical bone.

In one embodiment, in the fully pivoted position, the bottom edge 224 of the inner sleeve 220, like the bottom edge 214 of the outer sleeve 210, does not extend below a bottommost surface of the housing 110 and therefore does not impinge upon the cranial surface (cortical bone). As can be seen from the figures, when the drill guide sleeve assembly 200 pivots about axis 211, a portion (e.g., one half) of each of the outer sleeve 210 and the inner sleeve 220 pivots downwardly toward the cortical bone and therefore, in one embodiment, at least one of and preferably both of the outer sleeve 210 and the inner sleeve 220 can be contoured so as to not impinge upon the cortical bone in this pivoted position.

As shown in the cross-sectional view of FIG. 10, in the fully extended position, the bottom edges of both the inner sleeve 220 and outer sleeve 210 are located within or above the plane that contains the bottom surface of the housing 110 including the extension 180. This is a result of the upwardly sloped surfaces 213, 225 along the portions of both the inner sleeve 220 and the outer sleeve 210 that pivot downward towards the bottom surface of the housing 110 and the cranium when the drill guide sleeve assembly 200 pivots. As shown, the flat portions of the inner sleeve 220 and outer sleeve 210 that are opposite to the upwardly sloped arcuate portions are in a raised position relative to the bottom of the housing 110 once again due to the pivoting motion and the direction of rotation. It will be appreciated that by tailoring the shape of the bottom edges of the inner sleeve 220 and the outer sleeve 210, these structures do not contact and burrow into the cranium during the entire travel between the fully retracted position and the fully extended position, as well as when the drill guide sleeve assembly 200 is in the fully extended position which represents the maximum degree of pivot.

Similar to the shape of the bottom edge 214 of the outer sleeve 210, the bottom end (edge) 224 of the inner sleeve 220 is contoured in that the bottom edge is not contained in a single plane but instead, it includes a planar portion at one location and an upwardly sloped portion 225 at another location. This causes the bottom end 224 to be raised in one location (portion 225) relative to the other location as shown in the figures. When assembled to the outer sleeve 210, the portion 213 and the portion 225 are located adjacent one another. Thus, the upwardly sloped portions 213, 225 are located where there could be impingement with the cortical bone in the pivoted (fully extended) position of the drill guide sleeve assembly 200.

It will be understood that there are many cranial drill bits that are commercially available and therefore, the selection of the cranial drill bit 310 is based on a number of factors including but not limited to the anatomy of the patient, the location of the surgical site, etc. For example, cranial drill bits 310 come in different sizes and shapes, such as round, conical (which is described below), as well as other shapes.

Figure 7:
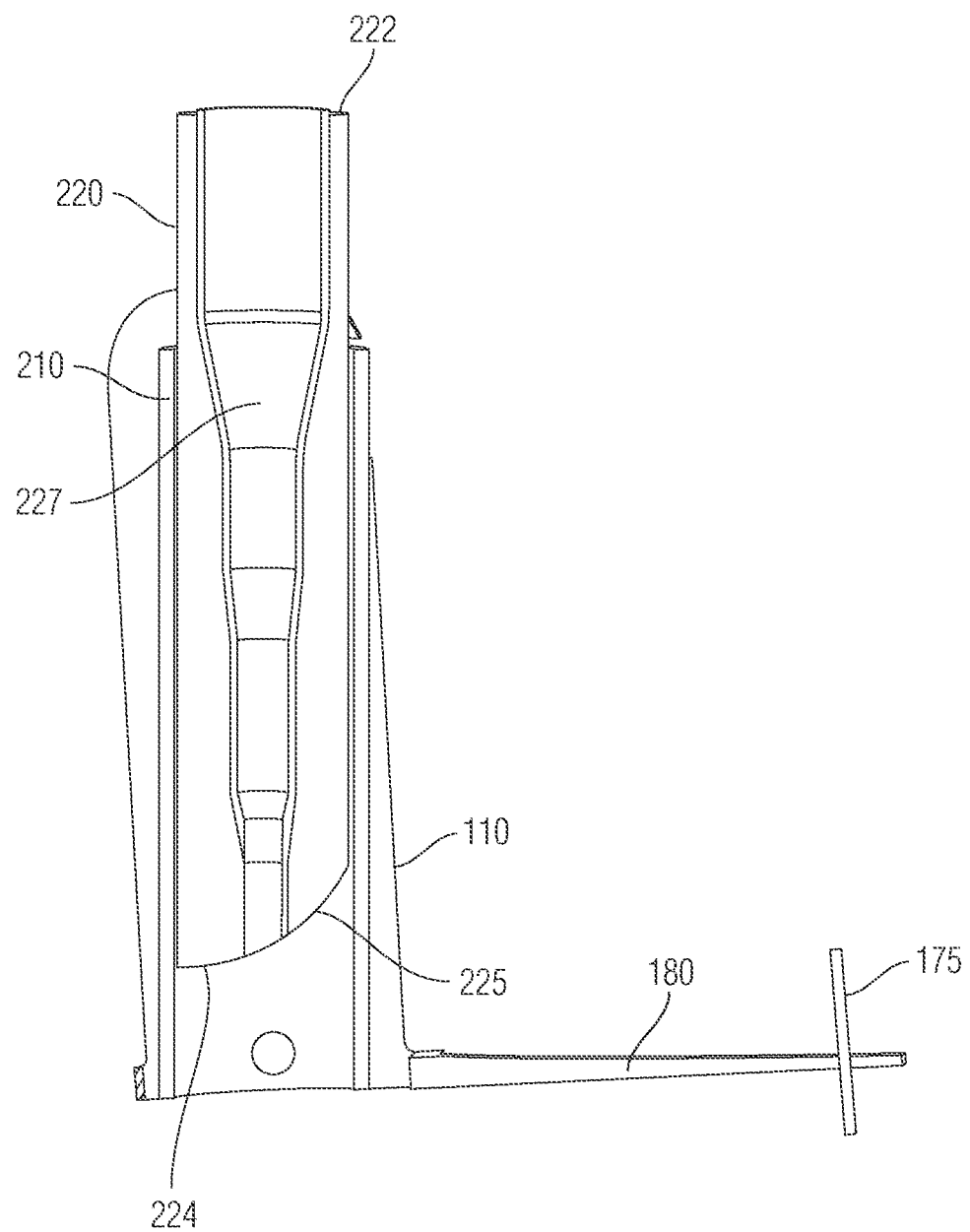
FIG. 7 is a cross-sectional view of the drill guide in the fully retracted position.
Figure 8:
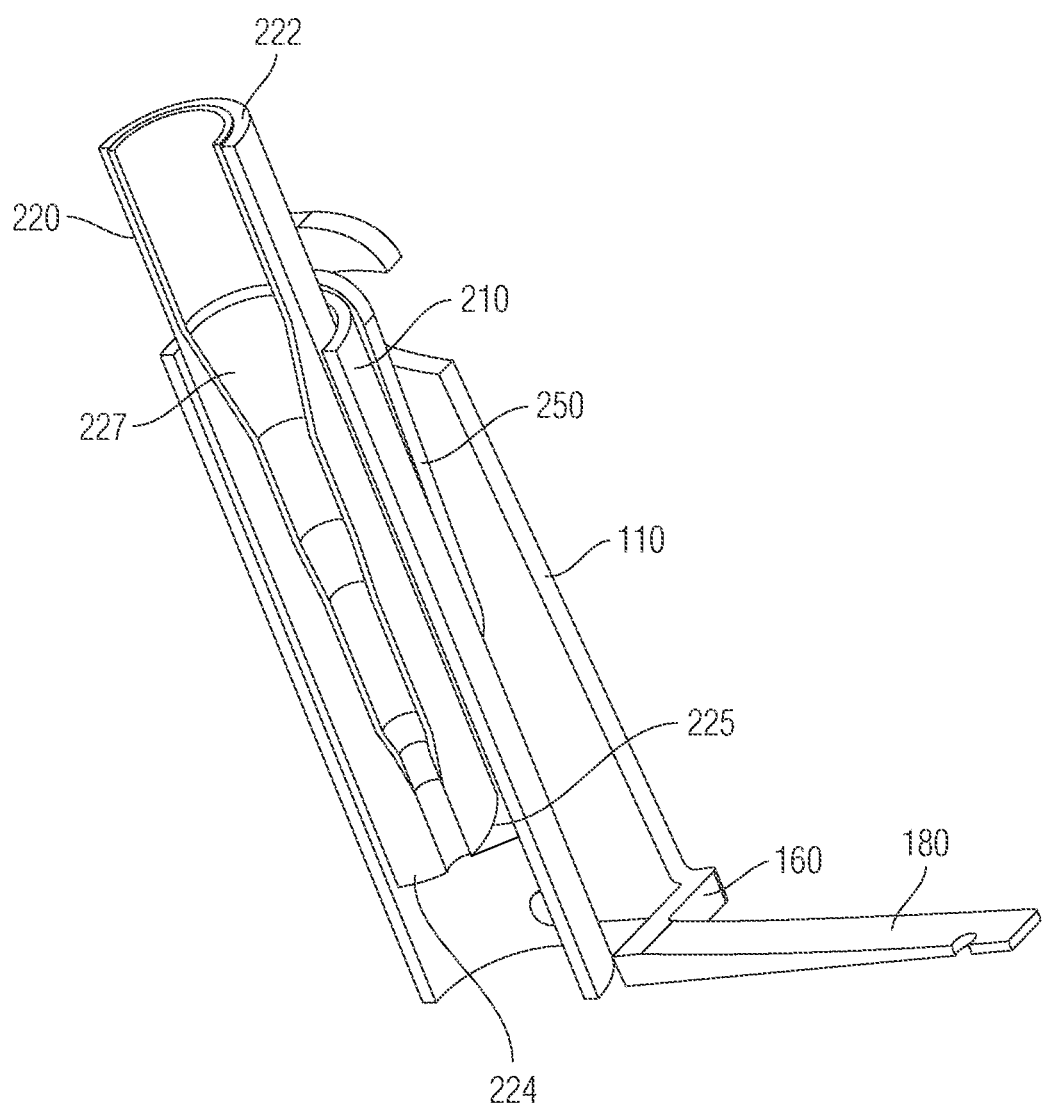
FIG. 8 is a cross-sectional perspective view thereof.
Figure 9:
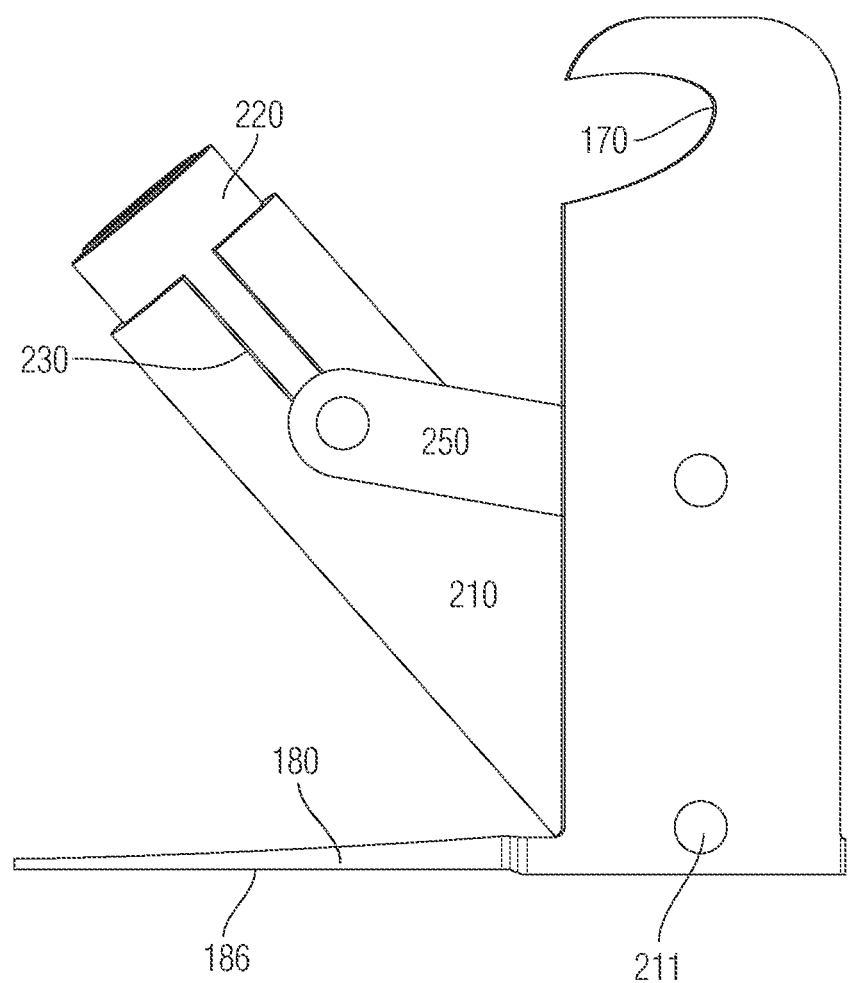
FIG. 9 is a side elevation view of the drill guide in a fully extended (fully pivoted) position.

As discussed herein and shown in FIGS. 7 and 8, in one embodiment, the lumen 227 (through bore) formed in the inner sleeve 220 is specifically formed in view of the shape of the drill 300 and in particular, the lower portion thereof. An exemplary cranial drill 300 will include a handle portion (not shown) and a lower portion 315 which can be thought of as being a lower shaft and/or chuck. The drill bit 310 extends downwardly from the lower portion 315.

The lumen 227 thus can have a variable diameter and in particular, as illustrated, the lumen can be divided into multiple sections that have different shapes and/or different diameters from one another. For example, the lumen 227 can be formed to have a mirror image compared to the shape of the drill shaft 315 and/or drill bit 310. Generally, as shown, the lumen 227 can have a progressively inward taper in that the top section of the lumen has the greatest diameter, while the bottom section has the smallest diameter. It will therefore be understood that the size and shape of the lumen 227 formed in the inner sleeve 220 can be customized in view of a specific intended drill guide/bit 310 and identified as such. This lends itself to the possibility that a kit can be provided with a plurality of different inner sleeves 220 each intended for use with one specific drill guide/bit 310 that can be identified on the outside of the inner sleeve 220. Much like a tool socket set, the kit can be provided in a case which can also readily identify the types of inner sleeves 220 included therein. In at least one embodiment, the inner sleeve 220 can be interchanged relative to the drill guide sleeve assembly 200 by simply removing pins 260 that attach the links 250 to the inner sleeve 220 and then interchanging the inner sleeve 220 and then reassembling.

Accordingly, a lumen 227 of the inner sleeve 220 can be thought of as being a negative impression of the drill shaft 315/bit 310 that is inserted therein such that when the drill shaft 315/bit 310 is inserted into the lumen, an intimate fit results when the drill guide is moved to a maximum down position (maximum advanced position). This creates in effect a stop that prevents unintended advancement of the drill 300 in the direction toward the patient's head.

Conical Shaped Drill Bit

Figure 13:
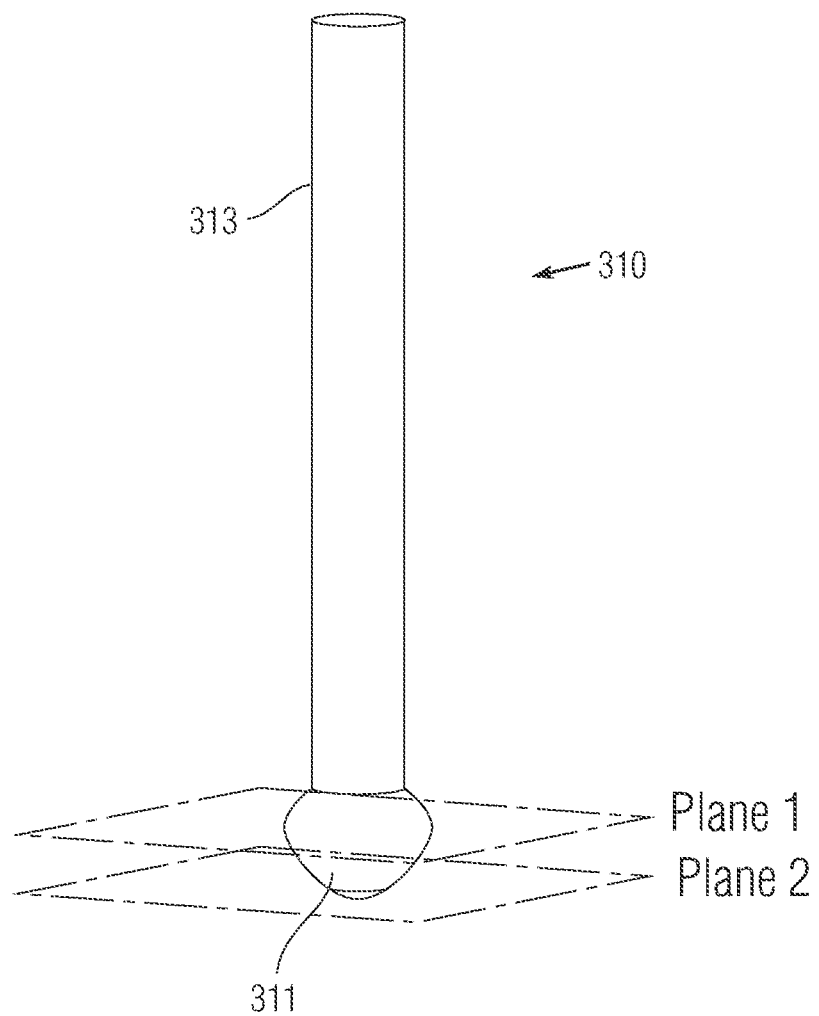
FIG. 13 is a side perspective view of a drill bit.
Figure 14:
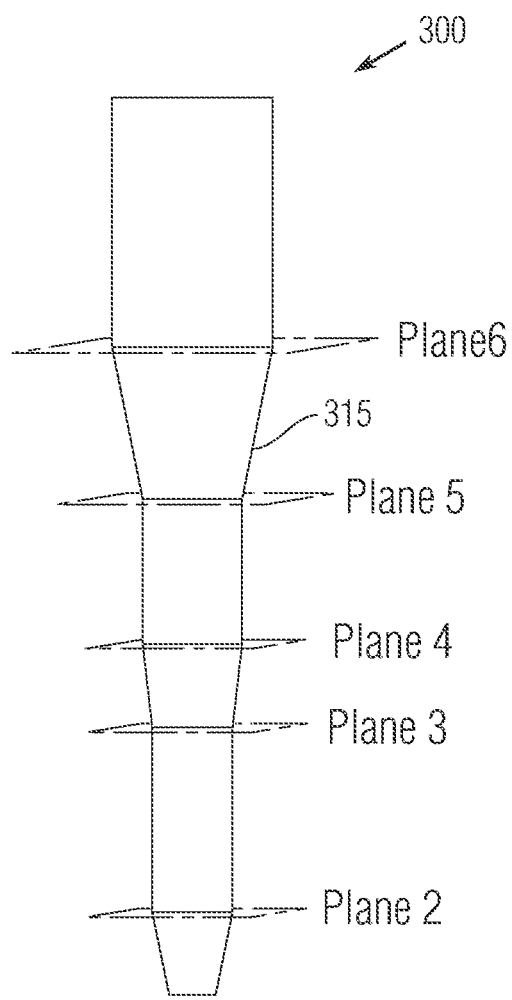
FIG. 14 is a side elevation view of a lower portion of a cranial drill that mates with the drill bit of FIG. 13.

As shown in FIGS. 10 and 13, in accordance with one embodiment, the drill bit 310 can be a conical shaped drill bit (inverted cone shaped). As shown, the drill bit 310 has a conical shaped distal end portion 311 and an elongated shaft 313 that can be or is securely fastened to the drill 300 and in particular, to a drill guide or drill shaft 315. In one embodiment, the drill bit 310 is removably attached to the drill 300 at a drill shank or drill guide shaft 315. Alternatively, the drill bit 310 can be permanently attached to the drill 300 and is not intended to be freely removable from the drill 300. In this case, the lumen of the inner sleeve 220 is configured in view of the lower portion of the drill 300 including the drill bit 310.

The length of the elongated shaft 313 can vary depending upon a number of parameters including the overall length of the drill bit 310, the length of the conical shaped distal end portion 311, the length of the drill guide 315, the length of the inner sleeve 220, etc. As will be appreciated, the conical shaped distal end portion 311 must pass through the inner sleeve 220 and therefore, the maximum diameter (width) of the conical shaped distal end portion 311 can be less than the inner diameter of the inner sleeve 220 to allow passage thereof. Alternatively, if the conical shaped distal end portion 311 has a diameter greater than the diameter of the lower end of the lumen of the inner sleeve 220, the shaft 313 can be fed into the lower end of the lumen within the inner sleeve 220 with the conical shaped distal end portion 311 being disposed below the inner sleeve 220 and then can be connected to the drill guide 315 as by a releasable connection.

In step eight, the hole (having an inverted cone shape) is drilled through the cranium by advancing the drill bit 310 within the inner sleeve 220 due to the pivoting of the drill guide sleeve assembly 200 as discussed herein. In one embodiment, the drill 300 is "fully loaded" within the inner sleeve 220 prior to movement of the drill guide sleeve assembly 200 between the fully retracted position and the fully extended position. In this fully loaded position, the distal tip of the drill bit 310 is preferably located just above the cranium (i.e., it is at this point free of contact with the cranium). In other words, the distal end of the drill bit 310 can lie below the bottom end of the inner sleeve 220 but not below the bottom of the base 110 since the drill bit 310 does not create an interference (with the cranium) in the at rest (fully retracted) position.

As described herein, according to at least one embodiment, the pivoting motion of the drill guide sleeve assembly 200 to the fully extended position, causes the drill bit 310 and driving of the drill bit 310 into the cranium due to the lowering of the inner sleeve 220 within the outer sleeve 210. Since the drill guide is intimately inserted and held in place within the inner sleeve 220, the drill guide moves with the inner sleeve 220 as the inner sleeve 220 is driven downward due to pivoting of the drill guide sleeve assembly 200.

As also discussed herein, the drill guide sleeve assembly 200, the drill bit 310 and the drill 300 are all selected in view of one another and are intended to complement one another and are designed to control the movement of the drill bit 310. In particular, the length of the drill bit 310 and the length of the drill guide sleeve assembly 200 are selected in view of one another and more particularly, since these two lengths are known, it can be calculated how much of a distal end portion 311 (drill portion) of the drill bit 310 extends beyond the bottom end (e.g., either the end 224 of the inner sleeve 220 or end 214 of the outer sleeve 210) through the cranium (cortical bone). Since the angle at which the inner sleeve 220 is set is known (when the drill guide sleeve assembly 200 is in a fully pivoted position) and the cortical bone thickness can be calculated (e.g., as by preoperative imaging or can be estimated or otherwise calculated), the user can select the drill bit 310 that provides the proper distal end portion length of the drill bit that provides sufficient length to drill through the cortical bone but does not continue therebelow into adjacent delicate structure (dura mater). The lumen 227 of the inner sleeve 220 can also be constructed, as discussed herein, so that full insertion of the drill guide into the lumen positions the distal end of the drill bit 310 at the desired location so that the degree of axial movement of the inner sleeve 220 within the outer sleeve 210 translates into the drill bit 310 being driven through the cranium and in particular, the drill bit 310 is driven a distance that passes through the cranium but does not damage underlying tissue/matter below the cranium.

More specifically, when the lower portion of the drill 300 is fully inserted into the inner sleeve 220, the conical shaped distal end portion 311 can be fully exposed below the bottom end of the inner sleeve 220 since this portion represents the portion that cuts through the cortical bone (cranium). The length of the conical shaped distal end portion 311 and/or length of the shaft 313 is thus selected in view of the thickness of the cortical bone through which the angled burr hole is formed. The conical shaped distal end portion 311, with its pointed tip, minimizes any contact between the distal end portion 311 and the dura mater below the cranium (cortical bone) through which the angled burr hole is formed in the event that the pointed tip extends below the cranium.

Stabilization Mechanism

Figure 15:
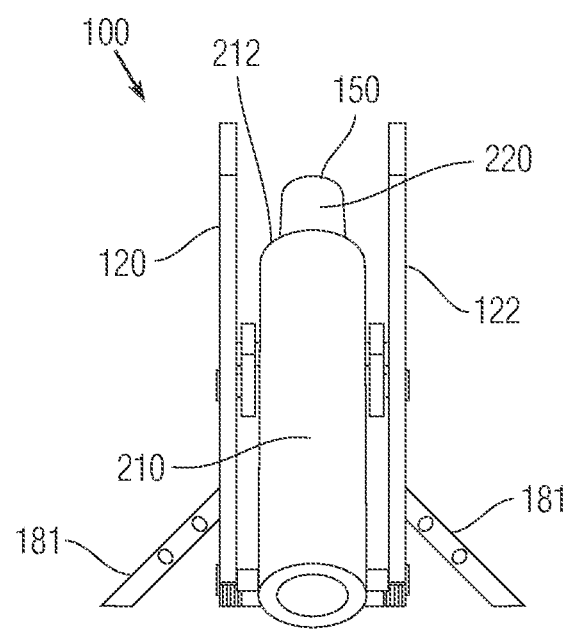
FIG. 15 is a front elevation view of illustrating a pair of stabilization members.

In accordance with one embodiment and as generally shown in FIG. 15, the drill guide 100 can include an additional stabilization mechanism (besides finger 180) to ensure the drill guide 100 is maintained in a stable position on the conical bone of the patient.

For example, the additional stabilization mechanism for the drill guide 100 can be in the form of extendable (deployable) legs 181 that are coupled to the drill guide 100, such as being coupled to the housing 110. In one embodiment, there are at least two deployable stabilization legs 181 that are opposite to one another and in another embodiment, there are three or more deployable stabilization legs 181 (e.g., a tripod configuration of legs). In order to ensure that the deployable stabilization legs 181 remain in the deployed position and seat against the cortical bone, a biasing mechanism can be employed and is configured to apply a biasing force to each deployable stabilization leg 181. For example, the biasing mechanism can be in the form of a spring that causes deployment of the stabilization legs 181.

In yet another embodiment, each of the deployable stabilization leg can have a variable length to allow for seating of the leg on the cranial surface since in the case of two opposing legs that are deployed against a curved surface, the distance to the cranial surface can differ from one leg to the other leg. Incorporating a telescoping function allows for variable length legs.

Once deployed (e.g., once moved from a storage position), the stabilization legs 181 provide additional stabilization points for the drill guide 100 on the cranial surface since they offer additional contact points between the drill guide 100 and the cranial surface.

A tripod type guide base for a cranial drill is commercially available and marketed as a Ghajar Guide® System. While this cranial drill guide is quite different than the drill guide 100 of the present invention, the Ghajar Guide® System uses a tripod structure for stabilization of the guide. A similar design can be incorporated into the drill guide 100 of the present invention.

Articulating Stabilization Mechanism

Figure 16:
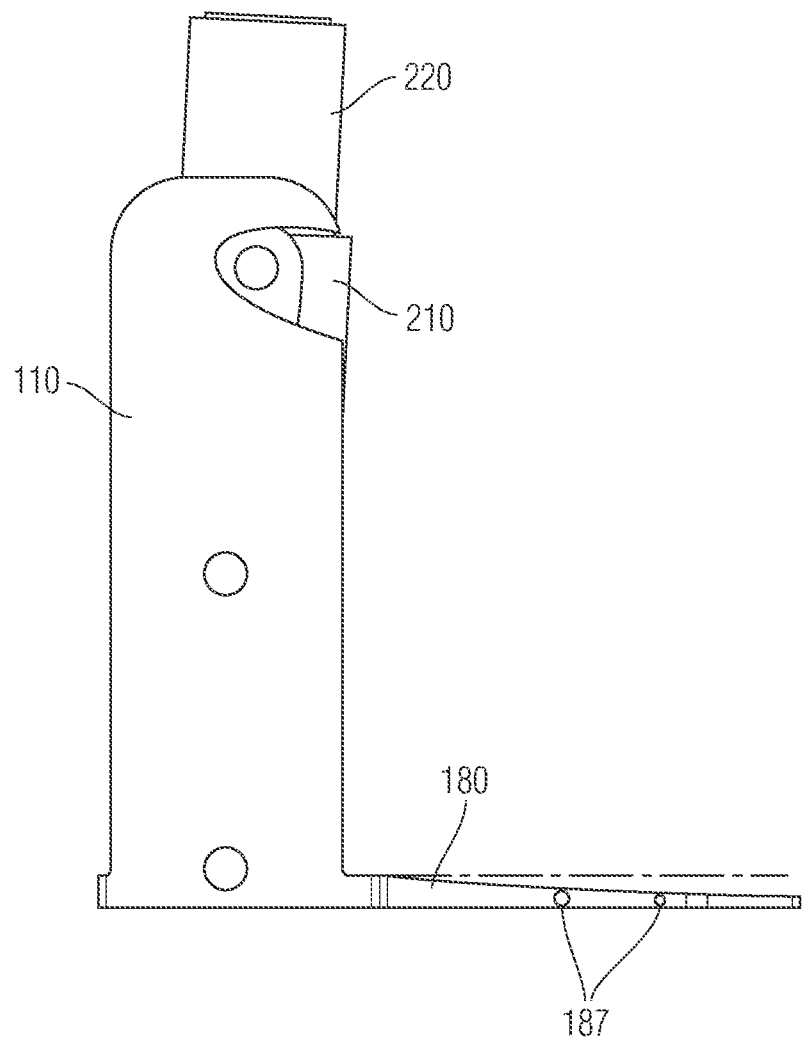
FIG. 16 is a side elevation view of a drill guide including an articulating stabilization member.

In another embodiment generally shown in FIG. 16, an articulated stabilization mechanism can be provided to allow improved positioning of the drill guide 100 on the skull of the patient. More particularly, it will be immediately recognized that the head is curved structure although there are portions that are more planar than others. In view of the curved nature of the skull, the stabilizing mechanism can therefore be configured to articulate so as to better fit the profile (curvature) of the head. For example, the stabilization finger 180 can be formed so as have one or more degrees of freedom (motion) and in particular, the stabilization finger 180 can be formed of two or more sections that are pivotally connected to allow one section to pivot relative to one or more other sections. For example, a hinge 187 can be formed adjacent sections to allow pivoting of one section relative to the other. The ability to incorporate one or more bends into the stabilization finger 180 allows it to better mirror the shape of the skull to which it is to be affixed.

It will be appreciated that other articulation mechanisms can equally be used to allow the stabilization mechanism (such as finger 180) to articulate to better fit the shape of the skull.

It will also be appreciated that the articulating stabilization mechanism can be biased, such as being spring biased, to assist in maintaining the articulating stabilization mechanism in a chosen position.

In yet another embodiment, the articulation mechanism is formed of a stabilization member, such as finger 180, that is formed of a plurality of articulating sections that are pivotable with respect to one another and there is a locking mechanism that allows for locking between the one or more articulating sections. For example, between adjacent sections there can be a lockable hinge that permits pivoting between the adjacent sections and once the adjacent sections are pivoted into a desired position, the hinge can be locked in place using the locking mechanism. For example, a locking screw or the like can be used to lock the hinge in place.

It will also be appreciated that in an embodiment, the articulating stabilization mechanism can be configured such that a portion thereof seats against the scalp while another portion thereof seats against the cortical bone.

Rotatable/Swivel Drill Guide Sleeve Assembly

Figure 19:
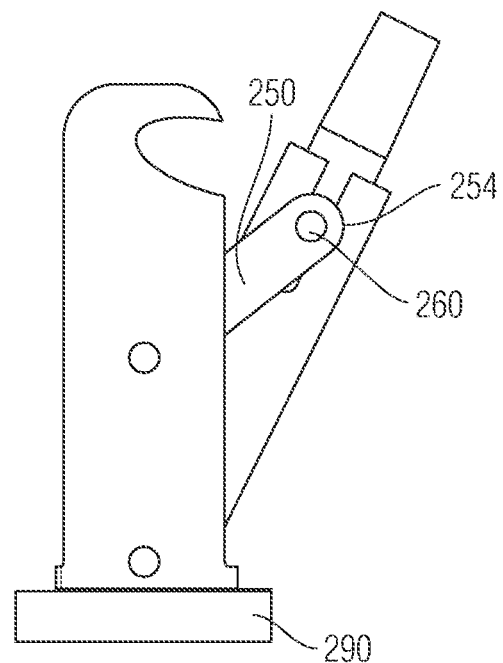
FIG. 19 is a side elevation of a drill guide having a rotatable base.

In another embodiment generally shown in FIG. 19, the housing 110 and the drill guide sleeve assembly 200 are part of a rotatable/swivel base 290 that is configured to seat against the cranial surface and also pivot to allow a position of the housing 110 and the drill guide sleeve assembly 200 to be changed in a rotational direction.

In particular, the base 290 can be an annular structure with a central hole that permits passage of the drill bit 310 through the drill guide sleeve assembly 200 and through the central hole to the cranial surface. Surrounding the central hole, the base 290 has a body that that can include one or more holes for receiving one or more fasteners (e.g., pins or screws) for securely attaching the base 290 to the cranial surface. This body portion of the base 290 extends radially beyond the housing 110 as shown. The housing 110 is also pivotally coupled to the base 290 using any number of different techniques. For example, the body of the base 290 can includes an annular shaped track formed between the central hole and the holes for receiving the fasteners. The bottom of the housing 110 can include complementary tabs or protrusions (e.g., flexible prongs with catches at their ends) that mate with and are captured within the track (e.g., as by a snap-fit) so as to couple the housing 110 to the base 290 in a rotatable manner. In particular, the base 290 is intended to be fixedly attached to the cortical bone as by insertion of the fasteners through the holes, while the housing 110 can rotate relative to the base 290 to allow rotational positioning of the housing 110 and the drill guide sleeve assembly 200 that is carried thereby.

By incorporating a swivel base into the drill guide 100, an inverted cone shaped burr hole can be formed through the cortical bone.

The present invention can be understood in view of the following Example(s) which are not limiting of the scope of the present invention but are merely exemplary thereof.

Example

In accordance with one exemplary embodiment, the drill guide 100 is used in the following manner for forming an angled burr hole through the skull as shown in the figures including FIGS. 17 and 18.

Figure 17:
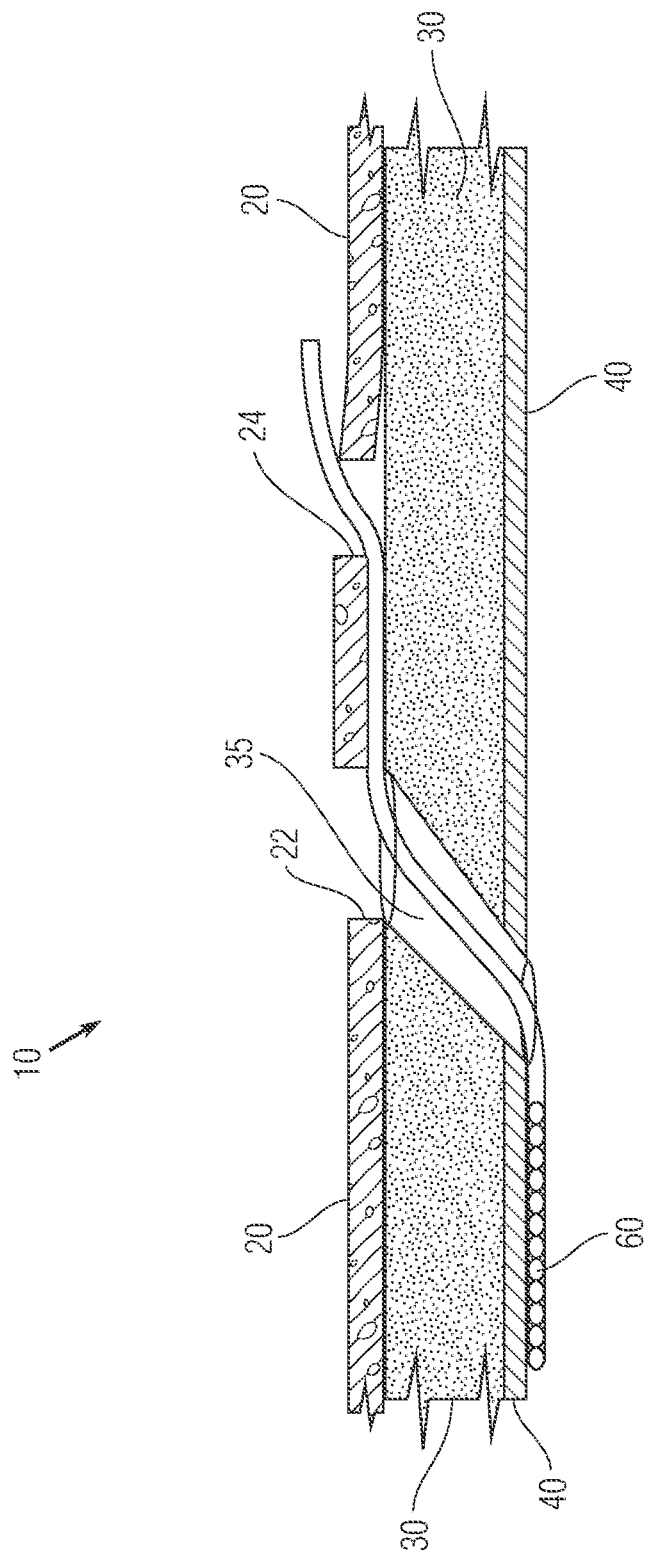
FIG. 17 is a cross-sectional view of a surgical site showing formation of an angled burr hole through cortical bone to allow insertion of an electrode underneath the cortical bone.
Figure 18:
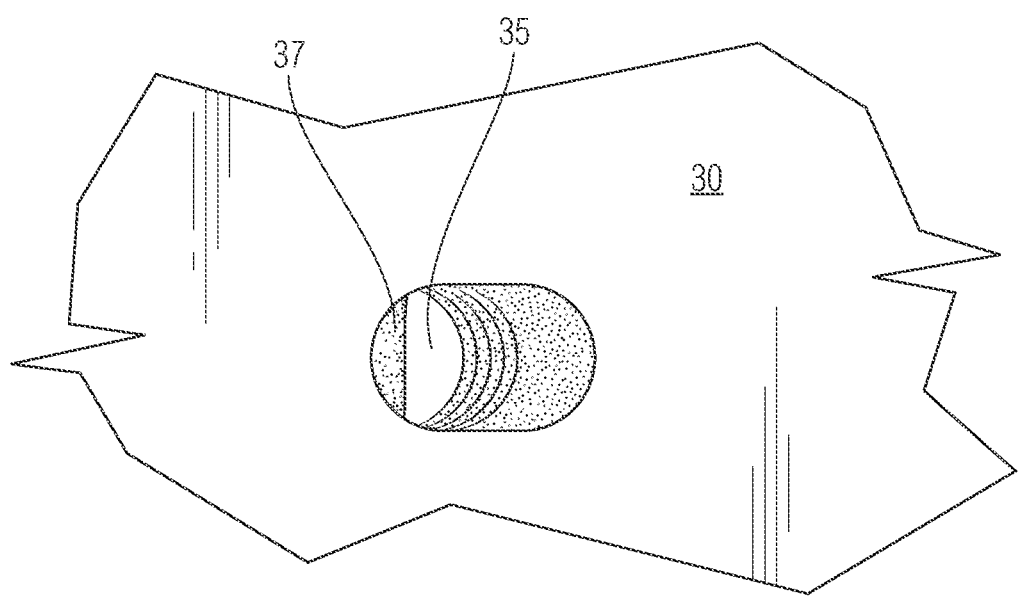
FIG. 18 is a plan view of a section of cortical bone showing formation of the angled burr hole.

FIG. 17 shows an exemplary surgical site 10 showing a cross-section of a person's head identifying a scalp 20, the underlying cortical bone (cranium) 30 and the underling dura mater 40.

The following procedure is capable of being performed using only local anesthesia at the patient's bedside or similar patient site as opposed to requiring a formal operating room (OR). In a first step, the surgical site can be prepared by shaving the surgical site and applying a local anesthesia to the surgical site 10 on the patient's head. The local anesthesia can be a dose of lidocaine, also known as xylocaine and lignocaine, is a medication used to numb tissue at the surgical site 10. In a second step, a first incision 22 (e.g., a first stab incision) is formed in the scalp 20 of the patient at a first location. As is known, the scalp 20 is the soft tissue envelope of the cranial vault. The scalp 20 consists of 5 layers: the skin, connective tissue, epicranial aponeurosis, loose areolar tissue, and pericranium. The scalp 20 is thus located above the skull bone 30 (cranium).

Any number of suitable tools can be used to form the first incision 22 including but not limited to suitable scalpels, etc. After the first incision 22 is formed, the scalp 20 can be pulled back to reveal the cortical bone 30 (skull bone or cranium) and in a third step, the drill guide 100 (FIG. 1) is inserted through the first incision 22 to the exposed cranium 30. In a fourth step, a second incision 24 is formed in the scalp 20 at a second location that is spaced from the first location. Like the first incision 22, the second incision 24 is formed using a suitable instrument/tool.

In a fifth step, the drill guide 100 is anchored to the cranium by inserting the stabilizing pin 175 (FIG. 7) which passes through the hole 185 (FIG. 1) of the finger 180. In the sixth step (which can occur before or after the fifth step), the drill bit 310 is inserted into the drill guide sleeve assembly 200 when it is in the at-rest upright position. The drill bit 310 is preferably inserted until the drill bit 310 reaches a stop point within the inner sleeve 220. At this position, the distal end of the drill bit 310 abuts or is in close proximity to the cranium or spaced a selected distance therefrom. The drill guide assembly 200 is then pivoted and as described herein, this pivoting action causes the inner sleeve 220 to be lowered within the outer sleeve, thereby causing the drill bit 310 to be driven into and through the cranium. The drill guide assembly 200 can be pivoted until it reaches its fully pivoted position. It will be appreciated that as shown in FIG. 18, the resulting hole formed through the cranium has a complex shape do to the drill bit 310 being not only driven forward but it also simultaneously undertakes a swept motion since the drill bit 310 is pivoting and moving in a lateral direction while being driven downward in a longitudinal direction.

It is also possible for the drill guide sleeve assembly 200 to be moved to the pivoted position (e.g., the fully pivoted position) whereby the drill guide sleeve assembly 200 is formed at an angle (other than 90 degrees) relative to the cranium 30. As discussed herein, once the drill guide sleeve assembly 200 is placed in the in-use position (the pivoted position), the drill bit 310 of the drill 300 is then inserted into the open top end 222. This would form a hole that is angled but does not have the complex shape shown in FIG. 18 since the drill bit is not advancing downward during the pivoting of the drill guide assembly. Thus, for sake of simplicity, the burr hole 35 in FIG. 17 is not shown to have the complex shape illustrated in FIG. 18; however, it will be understood that a burr hole having the shape of FIG. 18 would be formed when the drill bit 310 is first loaded into the inner sleeve 220 and then the entire drill guide assembly 200 is pivoted which causes the lowering of the drill bit into and through the cranium and the simultaneous swept motion (pivoting) of the drill guide assembly 200 causes the burr hole to be expanded in a lateral direction and ultimately, define an angled hole through the cranium.

Thus, in step six, the angled burr hole 35 is drilled through the cranium by pivoting the drill guide sleeve assembly 200 and it is the pivoting action and the lowering (axial movement) of the inner sleeve 220 within the outer sleeve 210 that causes the drill bit 310 to be advanced into and through the cranium since the drill guide/bit move in unison with the inner sleeve 220 and thus are lowered downward and since the bit 310 lies below the bottom edge of the inner sleeve 220, the drill bit 310 enters into and passes through the cranium, while the bottom edge of the inner sleeve 220 is preferably spaced from the cranium and in the fully extended position, the bottom edge of the inner sleeve 220 can be in close proximity to or in partial contact with the cranium.

As also discussed herein, the drill guide sleeve assembly 200, the drill bit 310 and the drill 300 are all selected in view of one another and are intended to complement one another and are designed to control the movement of the drill bit 310. In particular, the length of the drill bit 310 and the length of the drill guide sleeve assembly 200 are selected in view of one another and more particularly, since these two lengths are known, it can be calculated how much of the distal end portion (drill portion) of the drill bit 310 extends beyond the bottom end (e.g., either the end 224 of the inner sleeve 220 or end 214 of the outer sleeve 210) through the cranium 30. Since the angle at which the inner sleeve 220 is set is known and the cranium thickness can be calculated (e.g., as by preoperative imaging (e.g., x-ray) or can be estimated or otherwise calculated), the user can select the drill bit 310 that provides the proper distal end portion length of the drill bit 310 that provides sufficient length to drill through the cranium 30 but does not continue therebelow into adjacent delicate structure (dura mater 40). As described herein, the result of the drilling process is that an angled burr hole 35 is formed through the cranium 30.

In step seven, once the angled burr hole 35 is formed, the drill bit 310 is withdrawn from the drill guide sleeve assembly 200 and/or the drill guide assembly 200 is pivoted back to its original upright position and then the drill bit 310 is withdrawn. In step eight, the surgical site 10 is irrigated using an irrigation fluid that is passed to the surgical site 10 through the angled burr hole 35. As also discussed here, the drilling process can result in formation of an inwardly directed bone lip 37 at the bottom of the angled burr hole 35 due once again to the complex shape of the burr hole 35. This bone lip 37 can be removed in step eleven using any number of suitable techniques and suitable instruments/tools. For example, there are number of commercially available punch instruments that are configured to allow the user to grasp and remove the bone lip 37. For example, a rongeur is a strongly constructed instrument with a sharp-edged, scoop-shaped tip, used for gouging out bone and a popular type of a rongeur is a Kerrison Rongeur which is a manually operated instrument indicated for cutting or biting bone during surgery involving the skull or spinal column. For ease of illustration, the dura matter 40 is not shown in FIG. 18 below the opening 35.

In a ninth step, a catheter can be passed through the angled burr hole 35 into the dura mater 40 for delivery of an electrode 60, such as a strip electrode, to a target site that is within the dura mater 40 below the cranium 30. It will be appreciated that the second incision 24 formed in step four represents and defines an exit site for the implanted electrode 60 (e.g., the implanted strip electrode) since the proximal end of the implanted electrode 60 must be exteriorly accessible and therefor is routed outside of the patient's head.

As will be appreciated, the drill guide sleeve assembly 200 is configured to move in two distinct motions and in particular, the drill guide sleeve assembly 200 pivots about a first axis that passes through pins (posts) 211 and the inner sleeve 220 moves along a longitudinal axis of the outer sleeve 210 as a result of the inner sleeve 220 slidingly moving along a length of the outer sleeve 210. In accordance with the illustrated embodiments, the mechanism that coupled the drill guide sleeve assembly 200 to the housing 110 is configured such that the two distinct movements occur simultaneously in that as the drill guide sleeve assembly 200 pivots about the first axis, the inner sleeve 220 is caused to move along the longitudinal axis. For example, if the drill guide sleeve assembly 200 is pivoted in a direction away from the side walls 130, 140, the inner sleeve 220 moves downwardly within the outer sleeve 210 and conversely, if the drill guide sleeve assembly 200 is pivoted in a direction toward the side walls 130, 140, the inner sleeve 220 moves upwardly within the outer sleeve 210. The linkages 250 ensure that the pivoting motion of the drill guide sleeve assembly 200 is directly translated into simultaneous axial movement of the inner sleeve 220 within the outer sleeve 210.

Drill Sleeve Assembly with Depth Adjustment Mechanism

FIGS. 20-32 illustrate a cranial drill guide 400 that is similar to the cranial drill guide 100 and therefore like elements that are presented in both guide 100 and guide 400 are numbered alike. For example, the cranial drill guide 400 includes the housing 110 that has opposing side walls 130, 140 with each side wall 130, 140 including a notch 70 that functions in the same manner as in the drill guide 100

As with the drill guide 100, the drill guide 400 includes a movable drill guide sleeve assembly 201 that is similar to the movable drill guide sleeve assembly 200 with the difference between the two assemblies being discussed below. The drill guide sleeve assembly 201 is configured to guide the drill bit 310, as well as a lower portion 301 (FIG. 25), of the high speed cranial drill 300. The drill guide sleeve assembly 201 is pivotally coupled to the housing 110 and is movable between at least two different positions. The drill guide sleeve assembly 201 includes the outer sleeve 210 that is pivotally attached to an inner face of each of the first side wall 130 and the second side wall 140 in the manner described hereinbefore with respect to the drill guide sleeve assembly 200.

As illustrated, the outer sleeve 210 is generally cylindrical in shape to accommodate the round drill bit 310; however, other shapes are equally possible. Any number of different types of coupling techniques can be used to pivotally couple the outer sleeve 210 to the housing 110 as discussed previously.

Similar to what is shown in FIG. 4, the bottom edge 214 of the outer sleeve 210 of the drill guide sleeve assembly 200 is preferably contoured to accommodate the operation of the drill guide sleeve assembly 201 as described herein in detail and as shown in FIG. 22. More particularly, the bottom edge 214 of the outer sleeve 210 is not contained in a single plane but instead, the bottom edge 214 contains a first portion that is contained within a single plane and a second portion which represents an upwardly sloped portion relative to the other portion. The upwardly sloped portion 213 is located where there could be impingement with the cortical bone in the pivoted (fully extended) position (See, FIG. 10).

The outer sleeve 210 has the pair of opposing slots 230 formed therein at a first (top) end of the outer sleeve 210. The slots 230 are thus 180 degrees apart and are open at the first end 212. Each slot 230 is closed ended (at an opposite second end) and extends in a linear manner.

The drill guide sleeve assembly 201 also includes an inner sleeve 420 that is similar to the inner sleeve 220. The inner sleeve 420 is thus configured so as to be axially movable within the outer sleeve 210 and can also be cylindrical in shape to accommodate the drill bit 310. The inner sleeve 420 can include an open top end (edge) 422 and an open bottom end (edge) 424.

Figure 30:
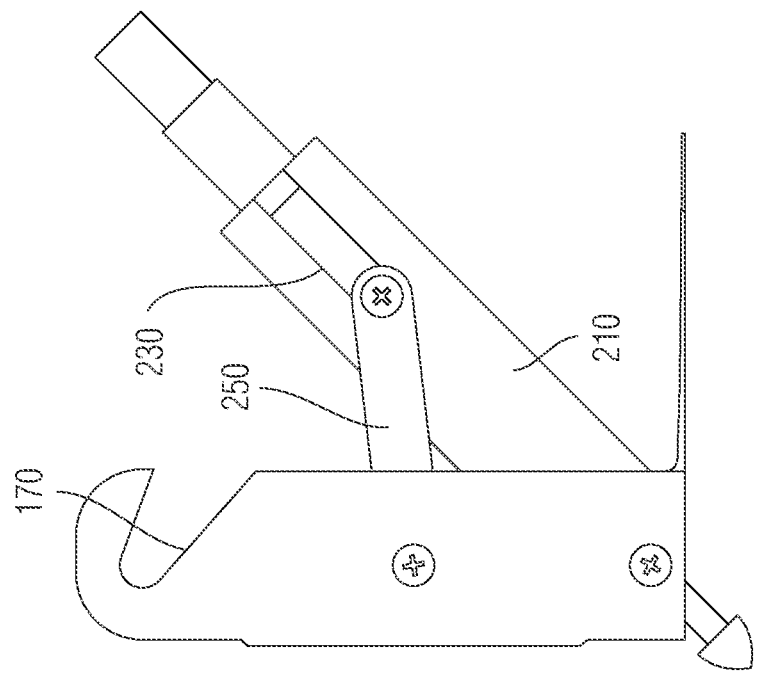
FIG. 30 is a side elevation view of the cranial drill guide in the fully extended position.

Unlike the inner sleeve 220 of the drill guide 100, the inner sleeve 420 of the drill guide 400 is part of a depth adjusting mechanism that allows the drill 300 to be properly positioned at a target depth within the inner sleeve 420 across all of the positions of the drill guide sleeve assembly 201 as it is pivoted from the fully retracted (upright) position of FIG. 20 to the fully extended position of FIG. 30.

As with the inner sleeve 220, the inner sleeve 420 is also pivotally coupled to the housing 110 by means of linkages 250. Ends of the two linkages 250 are pivotally coupled to the inner sleeve 220. More specifically, coupling members 260, e.g., pins or rivets, are formed as part of the inner sleeve 420 to connect the linkages 250 to the inner sleeve 420, with the coupling member 260 passing through the slots 230. The slots 230 thus allow access to the inner sleeve 420 that is contained within the hollow center of the outer sleeve 210. The closed end of the slot 230 defines a stop and thus defines a maximum degree of travel of pin 260. As will be appreciated in view of the figures, as the outer sleeve 210 pivots relative to the housing 110, the coupling members 260 ride within the slots 230 in a first direction when the outer sleeve 210 (and the contained inner sleeve 220) are pivoted in a first direction and in an opposite second direction when the outer sleeve 210 (and the contained inner sleeve 220) are pivoted in a second direction.

Figure 27:
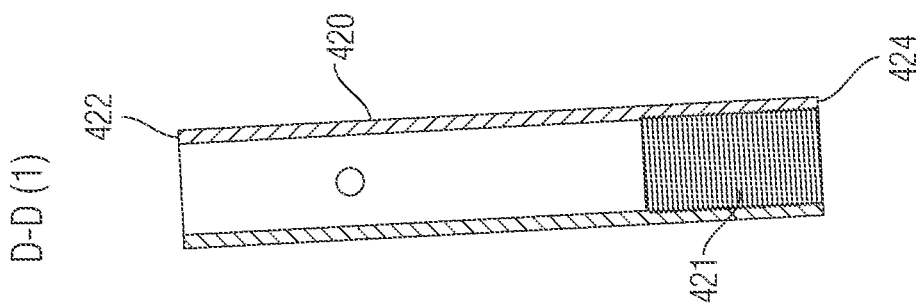
FIG. 27 is a cross-sectional view taken along the line D-D of FIG. 26.
Figure 26:
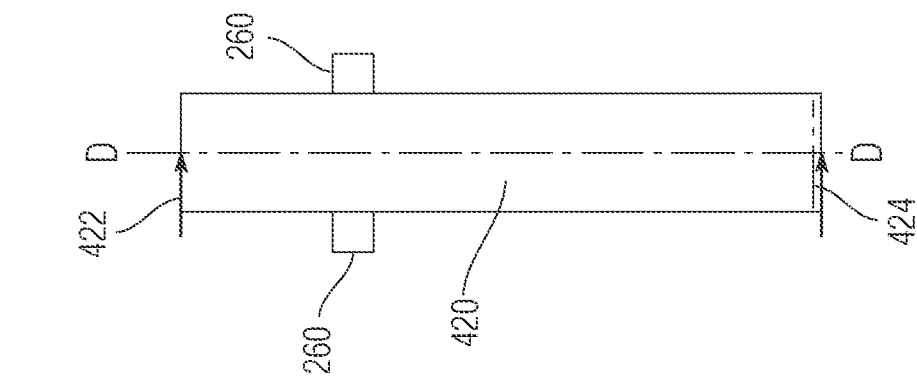
FIG. 26 is a side elevation view of an inner sleeve of the drill sleeve assembly.

FIGS. 26 and 27 further illustrate the inner sleeve 420 and more specifically, the inner sleeve 420 includes inner threads 421 that are formed proximate to and can extend to the bottom end 424 of the inner sleeve 420 as shown in FIG. 27. Any number of thread patterns can be used so long as the threads are complementary to the second set of threads discussed below. The axial length of the threaded portion (defined by the inner threads 421) is selected in view of the degree of axial depth adjustment that is desired as described below.

Figure 29:
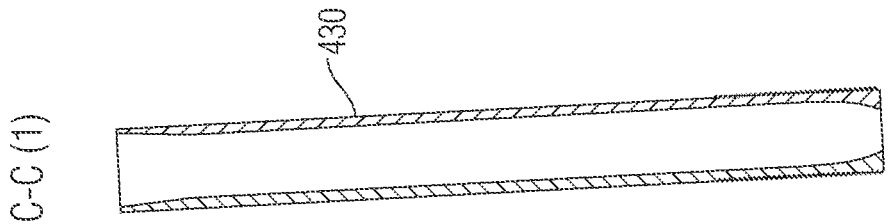
FIG. 29 is a cross-sectional view taken along the line C-C of FIG. 28.
Figure 28:
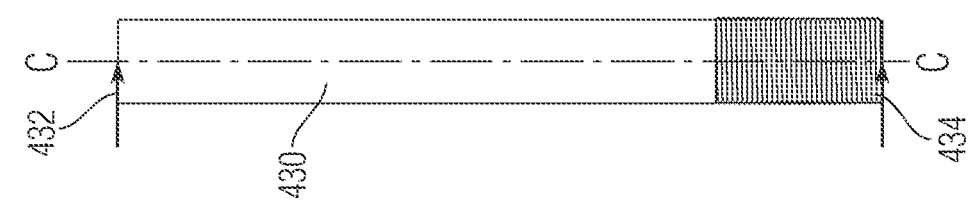
FIG. 28 is a side elevation view of a drill sleeve of the drill sleeve assembly.

The drill guide assembly 201 includes a drill sleeve 430 that is at least partially disposed within the hollow interior of the inner sleeve 420 and is coupled thereto. The drill sleeve 430 is shown in FIGS. 28 and 29 and like the other sleeves can be an elongated structure having a first open top end (edge) 432 and an open bottom end (edge) 434. The drill sleeve 430 is shaped and dimensioned so as to be received within the hollow interior of the inner sleeve 420 and thus, in the embodiment in which both sleeves 420, 430 are cylindrical structures, the outer diameter of the drill sleeve 430 is less than the inner diameter of the inner sleeve 420 to allow reception therein. The length of the drill sleeve 430 is preferably greater than the length of the inner sleeve 420 to allow the top end 432 to be accessible above the inner sleeve 420, when the two sleeves 420, 430 are mated together.

As best shown in FIG. 25, the hollow interior of the drill sleeve 430 can be contoured in view of the drill 300 and more particularly, the center lumen formed in the drill sleeve 430 can be inwardly tapered in the direction of the second end 434 so that the diameter (width) of the center lumen at the second end 434 is less than the diameter (width) of the center lumen at the first end 432. This tapered construction acts a stop for the axial advancement of the drill 300 within the drill sleeve 430 (an alternative stop (such as a step) could be used). When the drill 300 is advanced within the drill sleeve 430, the distal end of the drill body 300, from which the bit 310 extends, contacts the stop, the drill 300 has reached it maximum travel within the drill sleeve 430 (maximum depth of the drill body 300 within the drill sleeve 430).

Since the length of the drill bit 310 is known and the distance that it extends from the bottom end of the drill body 300 is known, and the location of the stop in the drill sleeve 430 is known, the drill sleeve 430 target position (location) within the inner sleeve 420 can be chosen (by threadingly moving the drill sleeve 430 within the inner sleeve 420) so as to result in the drill hit 310 advancing a preselected target distance from the bottom end of the inner sleeve 420 when the drill body 300 is at its fully inserted (maximum depth) within the drill sleeve 430. FIG. 25 shows such position. The relative fixed position of the drill sleeve 430 relative to the inner sleeve 420 is also selected in view of the degree of travel of the inner sleeve 420 relative to the outer sleeve 210

(i.e., the distance that the pin 260 can travel before striking the closed end of slot 230 which defines the end of travel and thus limits the axial movement of the inner sleeve 420 within the outer sleeve 210).

The drill sleeve 430 includes outer threads 433 that are formed proximate to and can extend to the bottom end 434 of the drill sleeve 430 as shown in FIG. 28. Any number of thread patterns can be used so long as the threads are complementary to the inner threads 421 since the threads 421, 433 are the means by which the two sleeves 420, 430 are engaged to one another. The axial length of the threaded portion (defined by the outer threads 433) is selected in view of the degree of axial depth adjustment that is desired as described below.

The threads 421, 433 provide a means by which the position of the drill sleeve 430 relative to the inner sleeve 420 can be set as by screwing the drill sleeve 430 into the inner sleeve 420 until the bottom end 434 of the drill sleeve 430 reaches a target location along the length of the sleeve 420. For example, in FIGS. 24 and 25, the bottom end 434 of the drill sleeve 430 is not located at the bottom end 424 of the inner sleeve but rather is spaced therefrom. Since the drill sleeve 430 is fixedly attached to the inner sleeve 420, when the inner sleeve 420 moves due to the pivoting movement of the outer sleeve 210, both the inner sleeve 420 and drill sleeve 430 are axially advanced within the outer sleeve 210 as a joined structure.

The above described depth adjusting mechanism thus allows the user to in effect set the degree upon which the drill bit 310 can be advanced below the drill guide 400 and thus, the degree of which the drill bit 310 can be advanced into the tissue. This allows the advancement of the drill bit 310 to be precisely controlled.

FIGS. 20-22 show the drill guide 400 in the fully retracted position and it can be seen that the drill guide sleeve assembly 201 is a raised position with the joined inner sleeve 420 and drill sleeve 430 in a maximum raised position. In this maximum raised position, the distal end of the drill bit 310 is fully contained within the outer sleeve 210 (as well as the inner sleeve 420) when the drill body 300 is fully inserted into the drill sleeve 430 until the drill body 300 contacts the internal stop. As a result, the distal end of the drill bit 310 does not apply a force to the cranial surface and the drill guide 400 is not lifted away from the cranial surface.

Figure 31:
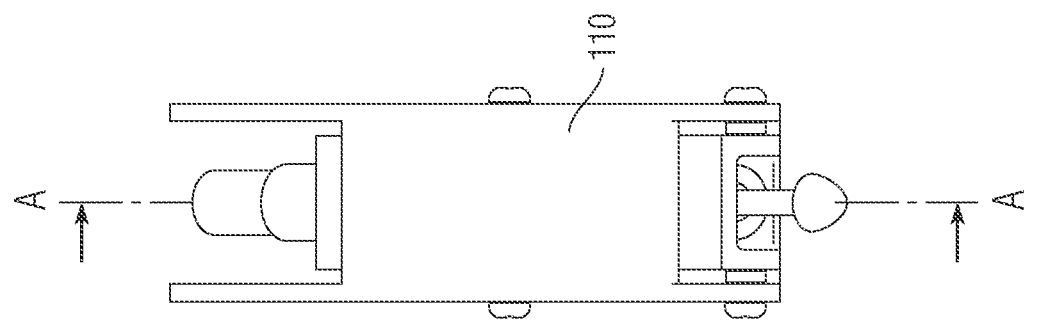
FIG. 31 is a rear elevation view thereof.

FIGS. 30-32 show the drill guide 400 in the fully extended position and it can be seen that the drill guide sleeve assembly 201 is a pivoted position with the joined inner sleeve 420 and drill sleeve 430 in a maximum pivoted position. In this maximum pivoted position, the distal end of the drill bit 310 is advanced downward and extends below the housing 110 and the outer sleeve 210 (as well as the inner sleeve 420). As a result, the distal end of the drill bit 310 is driven into the cranial surface in the manner described herein to form a drill hole of desired depth. As previously described, the depth of the hole is precisely controlled by the drill guide sleeve assembly 201 and in particular, the depth adjustment mechanism, described herein, can be employed to control and select the depth of the hole by controlling the degree to which the drill bit 310 extends below the housing 110. It will be seen and appreciated that during the movement from the fully retracted position (FIG. 20) and the fully pivoted position (FIG. 32), the drill body 300 is fully inserted into the drill sleeve 430 (i.e., the drill body 300 contacts the stop formed internally within the lumen of the drill sleeve 430 so as to form a press fit with the drill sleeve 430).

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:
1. A cranial drill guide comprising:
a housing; and
a drill guide sleeve assembly pivotally attached to the housing, the drill guide sleeve assembly having at least two degrees of freedom to allow the drill guide sleeve assembly to be moved to a first pivoted position for forming an angled burr hole through a cranial surface; wherein the drill guide sleeve assembly comprises an outer sleeve and an inner sleeve, the outer sleeve being pivotally coupled to the housing about a first pivot axis, while the inner sleeve moves axially within the outer sleeve in response to the pivoting of the outer sleeve.
2. The drill guide of claim 1, wherein the housing has a first side wall and a second side wall coupled to the first side wall with the drill guide sleeve assembly being disposed therebetween, wherein a cross member connects a bottom end of the first side wall to a bottom end of the second side wall with a pivot axis of the drill guide sleeve assembly being located above the bottom ends of the first side wall and the second side wall.

3. The drill guide of claim 1, wherein the two degrees of freedom comprise a pivoting motion of the drill guide sleeve assembly and an axial motion of a portion of the drill guide sleeve assembly.

4. The drill guide of claim 3, wherein pivoting of the drill guide sleeve assembly is translated into the axial motion of the portion of the drill guide sleeve assembly, wherein the pivoting and axial motion occur concurrently.

5. The drill guide of claim 1, wherein the inner sleeve is free of direct attachment to the outer sleeve but rather, the inner sleeve is pivotally coupled to the housing.

6. The drill guide of claim 1, further including a pair of pivotal linkages that are pivotally connected at a first end to the housing along a second pivot axis and at an opposite second end to the inner sleeve, whereby as the outer sleeve pivots about the first axis, the inner sleeve moves axially within the outer sleeve such that when the outer sleeve pivots in a first direction away from the housing, the inner sleeve is lowered within the outer sleeve, while when the outer sleeve pivots in an opposite second direction toward the housing, the inner sleeve is raised within the outer sleeve, wherein the second pivot axis is located above the first pivot axis.

7. The drill guide of claim 6, wherein the outer sleeve includes a pair of open ended slots formed therein, wherein coupling members that attach the linkages to the inner sleeve pass through the slots and move therein as the drill guide sleeve assembly pivots between a storage position and the first pivoted position.

8. The drill guide of claim 7, wherein in the first pivoted position, bottom ends of the inner sleeve and outer sleeve lie within or above a bottom plane of the housing, wherein the linkages are disposed external to the outer sleeve and the open ended slots are open at a top end of the outer sleeve.

9. The drill guide of claim 1, wherein the housing includes a stabilizing element that extends radially outward therefrom, the stabilizing element having a through hole for receiving a fastener for detachably securing the drill guide to the cranial surface.

10. The drill guide of claim 1, further including a base to which a bottom of the housing is rotatably mounted.

11. The drill guide of claim 1, wherein the drill guide sleeve assembly moves between a storage position in which the drill guide sleeve assembly is contained within the housing in an upright position and the first pivoted position, wherein in the storage position, the inner sleeve extends a maximum distance above a top end of the outer sleeve and in the first pivoted position, the inner sleeve extends a minimum distance above the top end of the outer sleeve or lies below the top end of the outer sleeve.

12. The drill guide of claim 1, wherein a bottom edge of each of the inner sleeve and the outer sleeve lies in more than one plane, the bottom edge of the outer sleeve having a flat portion and an upwardly sloped portion opposite the flat portion, each of the inner sleeve and the outer sleeve being oriented such that the upwardly sloped portion faces a pivot direction of the inner sleeve and the outer sleeve.

13. The drill guide of claim 1, wherein the inner sleeve includes an inner lumen, the inner lumen having a variable diameter.

14. The drill guide of claim 13, wherein the diameter of the inner lumen progressively decreases in a direction toward a bottom edge of the inner sleeve.

15. The drill guide of claim 13, wherein the inner lumen includes a plurality of discrete sections each having at least one of a different shape and different size relative to the one or more other section.

16. The drill guide of claim 15, wherein the inner lumen is constructed such that when the drill is fully inserted and the drill guide sleeve assembly is in a fully retracted position, a distal tip of the drill lies below a bottom edge of the inner sleeve.

17. The drill guide of claim 16, wherein a bottom edge of the outer sleeve has a flat portion and an upwardly sloped portion opposite the flat portion, the distal tip of the drill lying above the flat portion but below the upwardly sloped portion.

18. A cranial drill guide for guiding a drill comprising:
 a housing;
 a drill guide sleeve assembly pivotally attached to the housing, the drill guide sleeve assembly having at least two degrees of freedom to allow the drill guide sleeve assembly to be moved to a first pivoted position for forming an angled burr hole through a cranial surface; and
 a depth adjustment mechanism that is part of the drill guide sleeve assembly and is configured to set a maximum insertion position for the drill within the drill guide sleeve assembly and thereby permit a depth of the angled burr hole to be controlled;
 wherein the drill guide sleeve assembly comprises an outer sleeve, an inner sleeve, and a drill sleeve, the outer sleeve being pivotally coupled to the housing about a first pivot axis, while the inner sleeve and drill sleeve move axially within the outer sleeve in response to the pivoting of the outer sleeve.

19. The drill guide of claim 18, wherein the outer sleeve, inner sleeve and drill sleeve are coaxial to one another with the inner sleeve disposed within an inner lumen of the outer sleeve and the drill sleeve is disposed within an inner lumen of the inner sleeve.

20. The drill guide of claim 18, wherein the inner sleeve and the drill sleeve include engagement means that permits the drill sleeve to be fixedly coupled to the inner sleeve at a plurality of different axial positions with a top end of the drill sleeve being exposed above a top end of the inner sleeve across all of the plurality of different axial positions.

21. The drill guide of claim 18, wherein the inner sleeve includes inner threads at a lower portion of the inner sleeve and the drill sleeve includes outer threads at a lower portion of the drill sleeve, the drill sleeve being threadingly coupled to the inner sleeve.

22. The drill guide of claim 18, wherein the drill sleeve includes an inner lumen that extends along an entire length thereof, wherein the inner lumen includes a tapered end portion proximate a bottom end of the drill sleeve, the tapered end portion defining a stop for the drill.

23. The drill guide of claim 22, wherein the tapered end comprises an inward taper such that a diameter of the inner lumen is less at the bottom end of the drill sleeve compared to a diameter of the inner lumen at an opposite top end of the drill sleeve, the diameter of the inner lumen being selected such that a body of the drill cannot pass therethrough, while a drill bit extending distally from the drill body passes therethrough.

24. The drill guide of claim 22, wherein the drill guide sleeve assembly has a fully retracted position in which the drill guide sleeve assembly is configured to be positioned substantially perpendicular to the cranial surface and in the first pivoted position which comprises a fully extended position, the drill guide sleeve assembly is configured to be at an acute angle to the cranial surface, wherein in the fully retracted position, the inner sleeve and the drill sleeve is at a maximum raised position within the outer sleeve, while in the fully extended position, the inner sleeve and the drill sleeve is at a maximum lowered position within the outer sleeve, wherein a relative axial position of the drill sleeve and the inner sleeve in the maximum raised position is selected such that when a drill is fully inserted into the drill sleeve and contacts the stop, a drill bit of the drill is positioned proximate to a distalmost edge of a bottom end of the outer sleeve, while in the maximum lowered position, the drill bit extends below the outer sleeve and below the housing.

25. The drill guide of claim 24, wherein in the maximum raised position and in the maximum lowered position, a top end of the drill sleeve extends and protrudes above both top ends of the inner sleeve and the outer sleeve.

26. The drill guide of claim 18, wherein a bottom end of the outer sleeve includes an inwardly curved portion that is curved in a direction of a top end of the outer sleeve.

27. A method for forming an angled burr hole through a cranial surface comprising the steps of:
  positioning a cranial drill guide on the cranial surface, the drill guide having a pivotable drill guide sleeve assembly that is configured to receive a cranial drill;
  inserting the cranial drill within the drill guide sleeve assembly; and
moving the drill guide sleeve assembly from a first position to a first pivoted position, while the cranial drill is inserted within the drill guide sleeve assembly, resulting in a drill bit of the drill being automatically advanced into the cranial surface to form the angled burr hole through the cranial surface.

* * * * *